United States Patent
Franco

(10) Patent No.: US 8,556,931 B2
(45) Date of Patent: Oct. 15, 2013

(54) METHODS FOR IMAGING A DELIVERY SYSTEM

(75) Inventor: Ricardo Franco, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 523 days.

(21) Appl. No.: 12/328,468

(22) Filed: Dec. 4, 2008

(65) Prior Publication Data

US 2009/0156929 A1   Jun. 18, 2009

Related U.S. Application Data

(60) Provisional application No. 61/014,395, filed on Dec. 17, 2007.

(51) Int. Cl.
*A61B 17/08* (2006.01)
*A61D 1/00* (2006.01)

(52) U.S. Cl.
USPC ........................................................ 606/213

(58) Field of Classification Search
USPC ......... 606/108, 191, 192, 195, 198, 200, 213; 128/898; 623/1.11, 1.12; 600/407
See application file for complete search history.

(56) References Cited

U.S. PATENT DOCUMENTS

| | | | |
|---|---|---|---|
| 3,812,842 A | 5/1974 | Rodriguez | |
| 4,915,112 A | 4/1990 | Singer | |
| 5,095,911 A | 3/1992 | Pomeranz | |
| 5,192,302 A | 3/1993 | Kensey et al. | |
| 5,222,974 A | 6/1993 | Kensey et al. | |
| 5,304,184 A | 4/1994 | Hathaway et al. | |
| 5,419,324 A | 5/1995 | Dillow | |
| 5,674,231 A | 10/1997 | Green et al. | |
| 5,676,689 A | 10/1997 | Kensey et al. | |
| 5,860,923 A | 1/1999 | Lenker et al. | |
| 5,910,154 A | 6/1999 | Tsugita et al. | |
| 5,970,119 A | 10/1999 | Hofmann | |
| 6,078,832 A | 6/2000 | Lenker et al. | |
| 6,097,978 A | 8/2000 | Demarais et al. | |
| 6,142,987 A | 11/2000 | Tsugita | |
| 6,197,042 B1 | 3/2001 | Ginn et al. | |
| 6,344,044 B1 * | 2/2002 | Fulkerson et al. | 606/108 |
| 6,355,058 B1 | 3/2002 | Pacetti et al. | |
| 6,391,048 B1 | 5/2002 | Ginn et al. | |
| 6,450,976 B2 | 9/2002 | Korotko et al. | |
| 6,461,364 B1 | 10/2002 | Ginn et al. | |
| 6,623,510 B2 | 9/2003 | Carley et al. | |
| 6,635,082 B1 | 10/2003 | Hossainy et al. | |
| 6,719,777 B2 | 4/2004 | Ginn et al. | |

(Continued)

OTHER PUBLICATIONS

U.S. Appl. No. 61/014,395, filed Dec. 17, 2007, Franco.

(Continued)

*Primary Examiner* — Elmer Chao
(74) *Attorney, Agent, or Firm* — Workman Nydegger; Randy Shen

(57) ABSTRACT

A method for imaging a delivery system is disclosed. The method includes positioning an implantable device within a delivery apparatus. The implantable device has a first base material that includes a mixture of which a first radiopaque material is a component and/or coating at least a portion of the first base material with a coating of which a first radiopaque material is a component. The delivery apparatus may be positioned relative to an imaging device. An image produced by the imaging device may be analyzed. It may be determined whether the delivery apparatus is ready to deploy an implantable device.

20 Claims, 31 Drawing Sheets

(56) References Cited

U.S. PATENT DOCUMENTS

| | | |
|---|---|---|
| 7,054,476 B2 | 5/2006 | Oosawa et al. |
| 7,211,101 B2 | 5/2007 | Carley et al. |
| 7,670,369 B2 | 3/2010 | Schaeffer |
| 7,697,972 B2 | 4/2010 | Verard et al. |
| 2003/0204168 A1 | 10/2003 | Bosma et al. |
| 2004/0153122 A1 | 8/2004 | Palermo |
| 2004/0167596 A1* | 8/2004 | Richter .......................... 623/1.1 |
| 2005/0249776 A1 | 11/2005 | Chen et al. |
| 2006/0020332 A1 | 1/2006 | Lashinski et al. |
| 2006/0025681 A1 | 2/2006 | Abovitz et al. |
| 2008/0004686 A1 | 1/2008 | Hunt et al. |
| 2008/0009933 A1* | 1/2008 | Ta et al. ....................... 623/1.11 |
| 2008/0063304 A1 | 3/2008 | Russak et al. |
| 2010/0152572 A1 | 6/2010 | Mackiewicz |
| 2011/0034802 A1 | 2/2011 | Shrivastava et al. |

OTHER PUBLICATIONS

U.S. Appl. No. 61/138,448, filed Dec. 17, 2008, Mackiewicz.
U.S. Appl. No. 12/482,343, filed Dec. 6, 2011, Office Action.
U.S. Appl. No. 12/482,343, filed Apr. 3, 2012, Notice of Allowance.
U.S. Appl. No. 12/536,389, filed Feb. 29, 2012, Office Action.
U.S. Appl. No. 12/536,389, Apr. 12, 2012, Office Action.
U.S. Appl. No. 12/536,389, Sep. 10, 2012, Office Action.

* cited by examiner

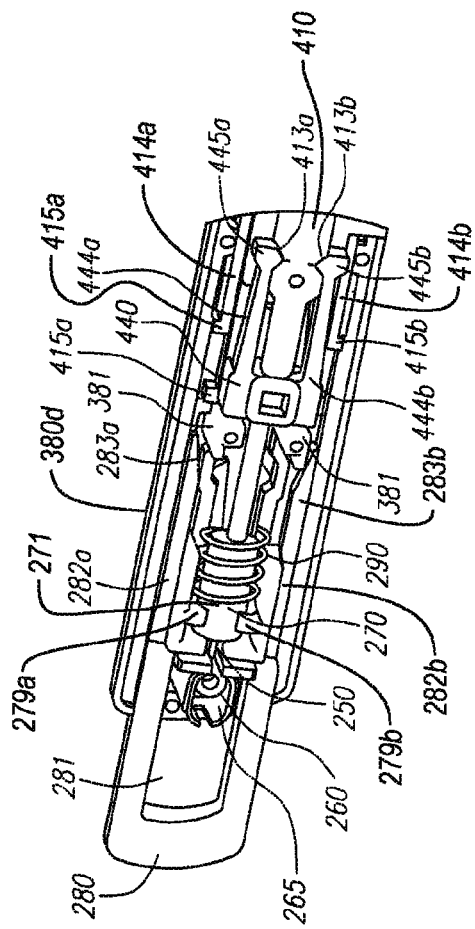
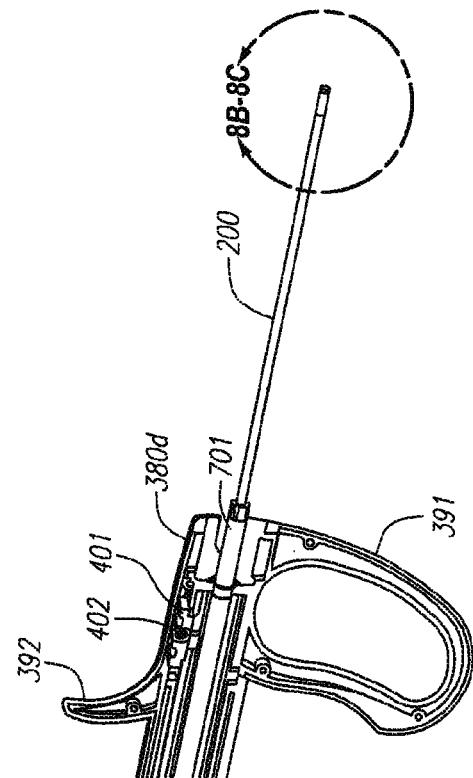
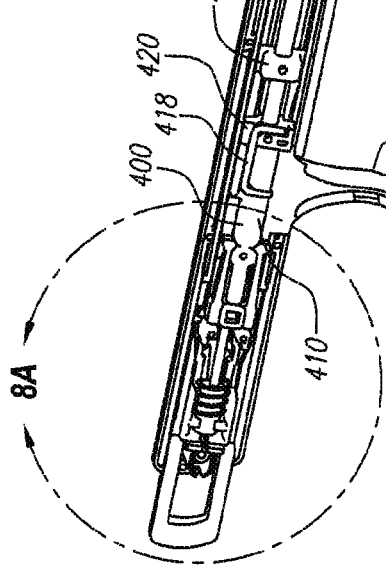

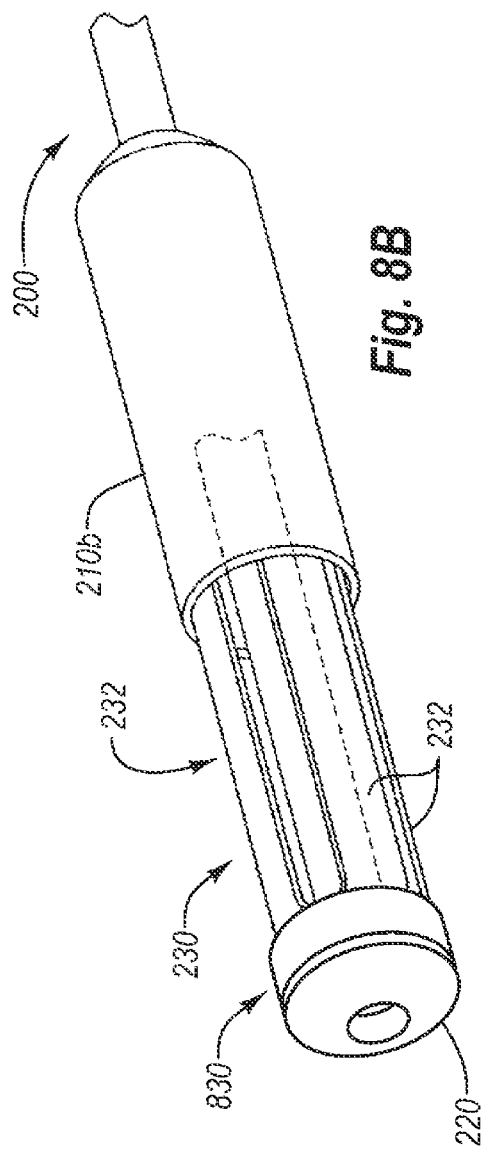
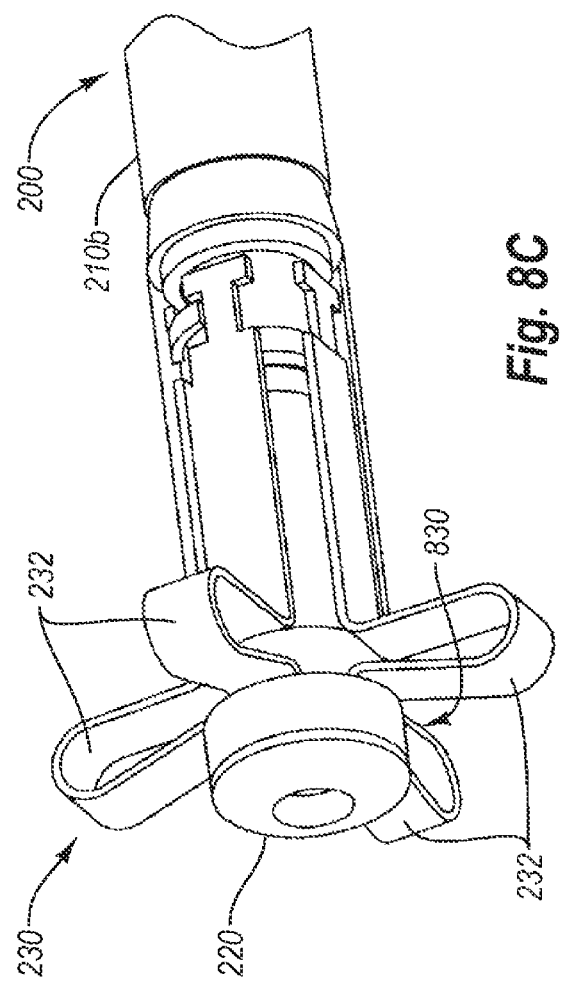

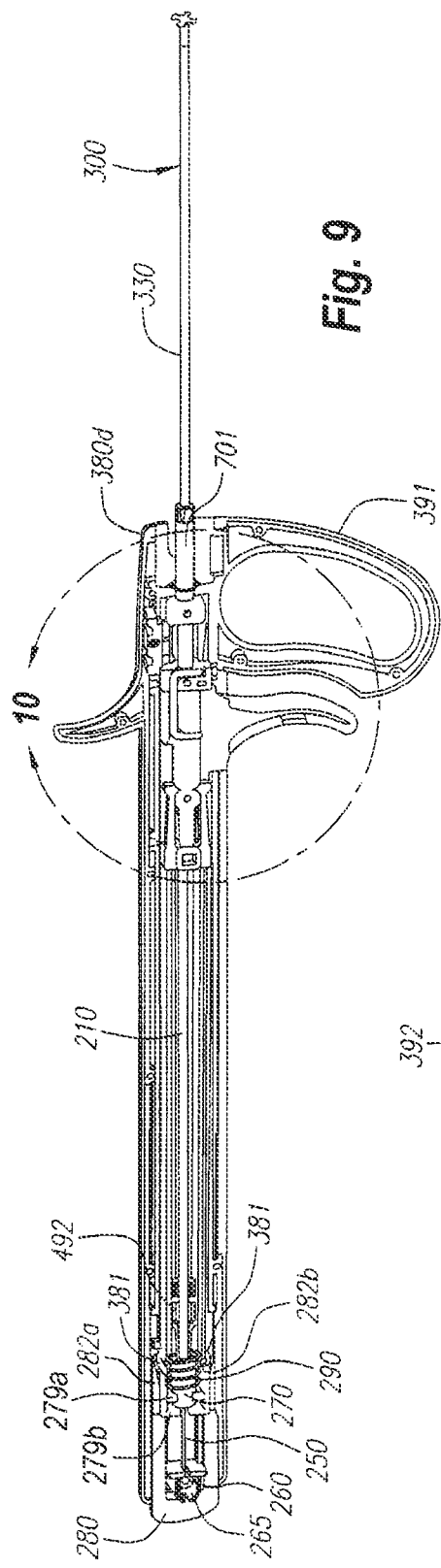
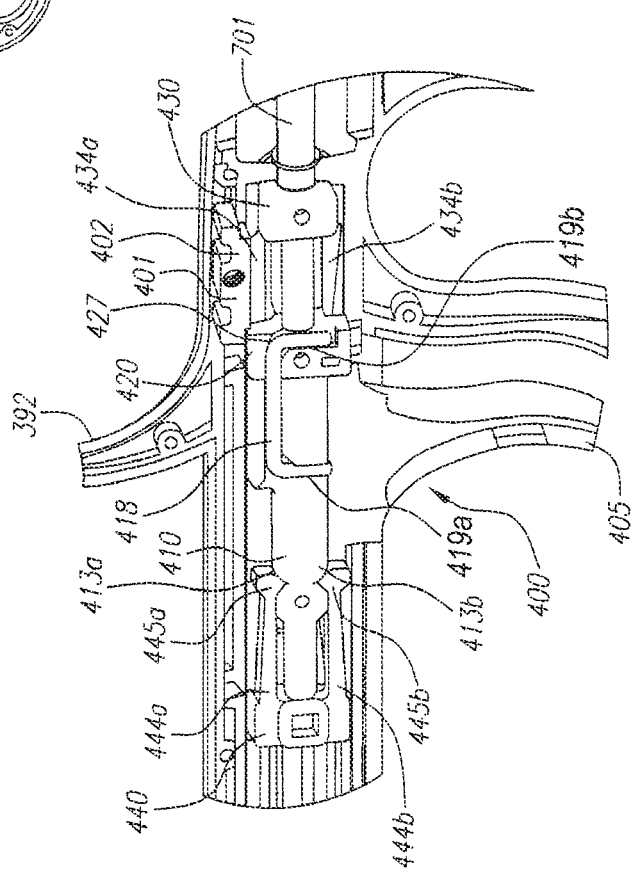
Fig. 9
Fig. 10

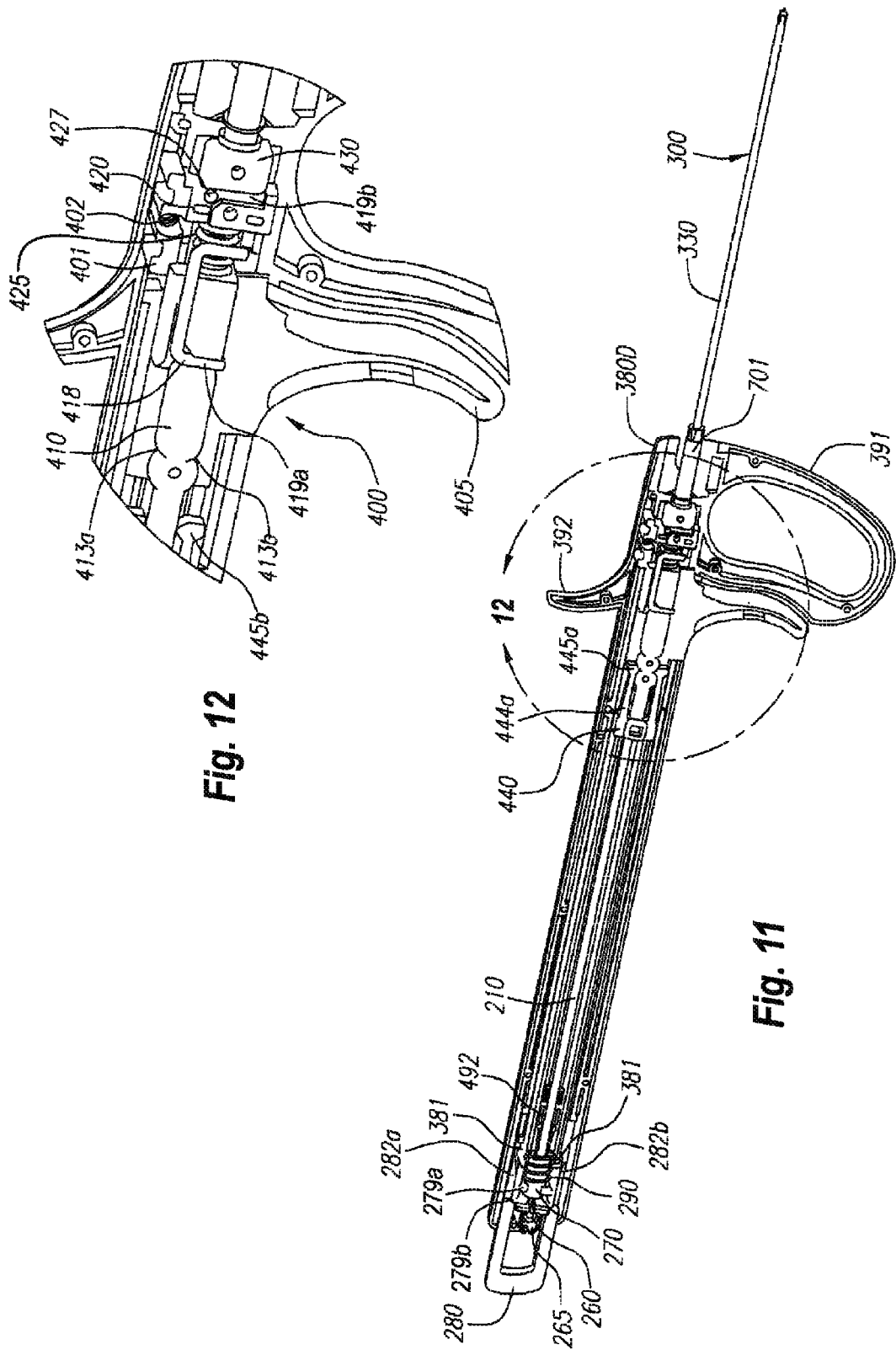

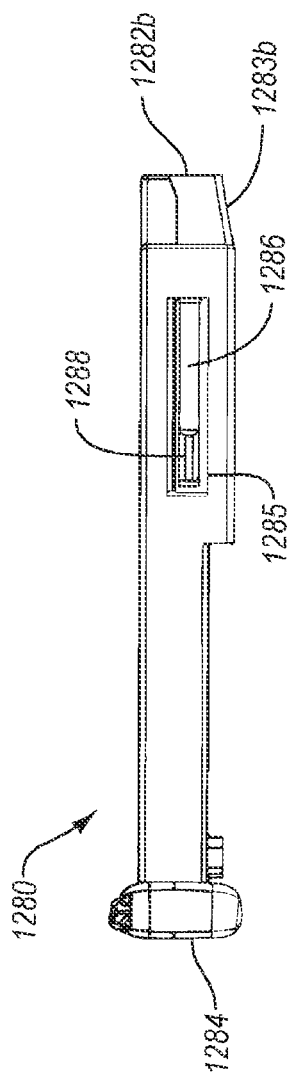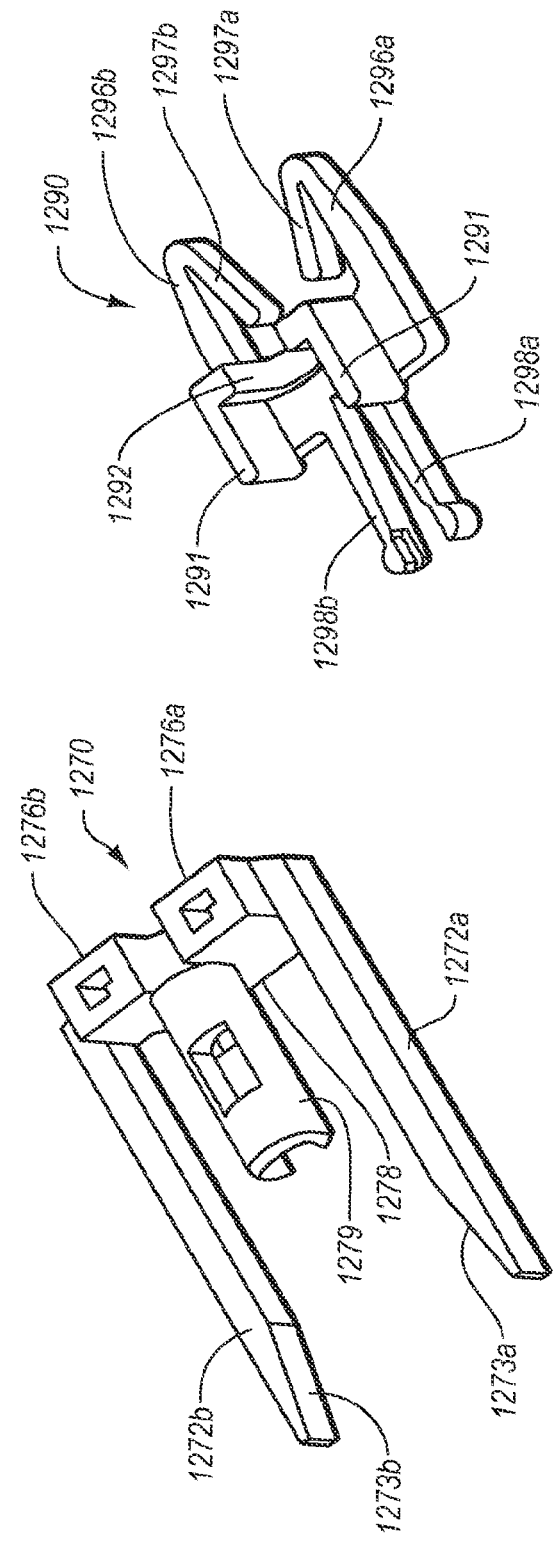

METHODS FOR IMAGING A DELIVERY SYSTEM

CROSS-REFERENCE TO RELATED APPLICATIONS

This application claims the benefit of and priority to U.S. Provisional Patent Application No. 61/014,395, filed Dec. 17, 2007, and entitled "Methods for Imaging a Delivery System" which is incorporated herein by reference in its entirety.

FIELD OF THE INVENTION

The present invention relates generally to medical devices. More particularly the present invention relates to methods for imaging a delivery system.

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure (for example, inserting a stent into a body lumen). Thus, the introducer sheath may facilitate introducing various devices into the vessel, while minimizing trauma to the vessel wall and/or minimizing blood loss during a procedure.

Upon completing the procedure, the devices and introducer sheath would be removed, leaving a puncture site in the vessel wall. Traditionally, external pressure would be applied to the puncture site until clotting and wound sealing occur, however, the patient must remain bedridden for a substantial period of time after clotting to ensure closure of the wound. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,689, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Accordingly, methods for manufacturing delivery systems may be useful. Furthermore, methods for observing delivery systems before, during, and/or after use may also be useful.

BRIEF SUMMARY

An embodiment of a method for imaging a delivery system is described. The method includes positioning an implantable device within a delivery apparatus. In one embodiment, the implantable device includes a first base material. The first base material includes a mixture of which a first radiopaque material is a component. In another embodiment, at least a portion of the first base material is coated with a coating of which the first radiopaque material is a component. The method includes positioning the delivery apparatus relative to an imaging device. The method includes analyzing an image produced by the imaging device. The method includes determining whether the delivery apparatus is ready to deploy the implantable device.

Another embodiment of a method for determining whether an implantable device is deployed is described. The method includes positioning a delivery apparatus relative to an imaging device. The delivery apparatus includes at least a portion that is capable of being imaged by an imaging device. The delivery apparatus includes an implantable device positioned within the delivery apparatus. The implantable device is capable of being imaged by an imaging device. The method includes analyzing a first image produced by the imaging device. The method includes determining the relative position of the implantable device within the delivery apparatus. The method includes at deploying the implantable device. The method includes positioning the delivery apparatus relative to the imaging device. The method includes analyzing a second image produced by the imaging device. The method includes determining whether the implantable device was deployed.

In some embodiments, determining whether the delivery apparatus is ready to deploy an implantable device includes determining the relative position of the implantable device within the delivery apparatus and determining whether the implantable device is properly positioned within the delivery apparatus. The method, in further embodiments, includes forming at least a portion of the delivery apparatus from a second base material and processing at least a portion of the delivery apparatus by providing a second base material that includes a mixture of which a second radiopaque material is a component and/or coating at least a portion of the second base material with a coating of which the second radiopaque material is a component.

Positioning the delivery apparatus relative to the imaging device, in some embodiments, includes aligning the delivery apparatus with at least one alignment indicator. After deploying the implantable device, in some embodiments, the position of the implantable device within the delivery apparatus is determined.

The portion of the delivery apparatus that is processed, in further embodiments, is at least one of a portion of a locator assembly and a portion of a carrier assembly. In further embodiments, the portion of the locator assembly that is processed is at least one of a portion of a tubular body and a portion of a control member. In still further embodiments, the portion of the tubular body that is processed is at least one of a portion of a distal end of the tubular body and a portion of an expansion end of the tubular body. The portion of the expansion end of the tubular body that is processed, in yet further embodiments, is a portion of at least one substantially flexible member of the expansion end. In some embodiments, the portion of the carrier assembly that is processed is a portion of a tube set.

In some embodiments, the first radiopaque material and the second radiopaque material are different materials. A second portion of the delivery apparatus is processed, in further embodiments, by providing a third base material that includes a mixture of which a third radiopaque material is a component and/or coating at least a portion of the third base material with a coating of which the third radiopaque material is a component. At least one of the first radiopaque material, the second radiopaque material, and the third radiopaque material, in some embodiments, have different radiopacities.

Other aspects and features of the present invention will become apparent from consideration of the following description in conjunction with the accompanying drawings.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIG. 7 illustrates the assembled carrier assembly and triggering assembly of the apparatus shown in FIGS. 6A and 6B;

FIG. 8A illustrates a close-up view of the proximal end of the apparatus shown in FIG. 7;

FIG. 8B illustrates a close-up view of the distal end of the apparatus shown in FIG. 7 in an unexpanded state;

FIG. 8C illustrates a close-up view of the distal end of the apparatus shown in FIG. 7 in an expanded state;

FIG. 9 illustrates the apparatus of FIG. 7 after distal advancement of the locator assembly, the triggering system, and the carrier assembly;

FIG. 10 illustrates a close-up view of the triggering system and carrier assembly of the apparatus shown in FIG. 9;

FIG. 11 illustrates the apparatus of FIG. 6A-6B after the clip has been released to close the opening in the tissue;

FIG. 12 illustrates a close-up view of the triggering system and carrier assembly of the apparatus of FIG. 6A-6B after the clip has been released to close the opening in the tissue;

FIG. 16D illustrates a side view of a plunger of the locator control system of FIG. 16B of the alternative embodiment of FIG. 14;

FIG. 16E illustrates a perspective view of a tubular body block of the locator control system of FIG. 16B of the alternative embodiment of FIG. 14;

FIG. 16F illustrates a perspective view of a spring retainer of the locator control system of FIG. 16B of the alternative embodiment of FIG. 14;

Figure 1:
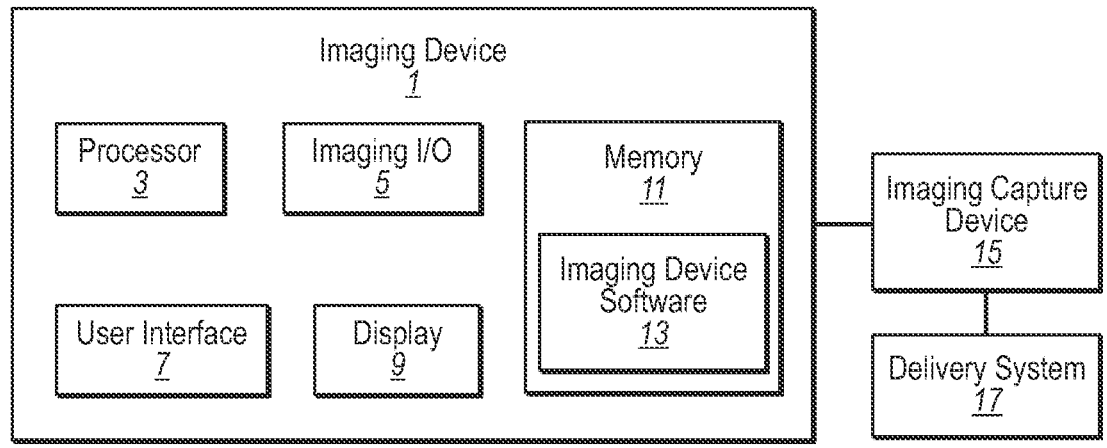
FIG. 1 illustrates an embodiment of an imaging device.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

The embodiments described herein extend generally to methods, systems, and apparatus for imaging a delivery system. By way of example only, a delivery system may include a delivery apparatus and an implantable device. For example, embodiments of implantable devices, such as closure elements and stents, and delivery apparatus, such as closure element apparatus and stent delivery apparatus, are disclosed.

Imaging a delivery system or any portion thereof can provide several advantages. The position of the implantable device with respect to the delivery apparatus prior to deployment can be evaluated. The expected operation of the delivery system can also be analyzed. For instance, the generated images can be used to identify potential obstructions or defects in the delivery system. Further, images of the delivery system can be at one or more stages of operation.

Thus, embodiments of the invention relate to methods for imaging a delivery system before, during, and/or after deployment and may be useful for determining the root causes of functional failures, determining the behavior of the apparatus during firing, and/or addressing customer complaints related to the failure of a delivery apparatus. Imaging can also be used to ensure that the delivery apparatus functioned as expected, for example, by ensuring that the implantable device was deployed.

FIG. 1 illustrates an embodiment of an imaging device 1. The imaging device 1 can generate an image of the delivery system and one or more points in time relative to the deployment or use of the delivery system. The imaging device 1 may include a fluoroscopic imaging device (for example, a high magnification x-ray imaging device) an ultrasonic imaging device, and/or other imaging devices. The imaging device 1 may include a processor 3. The processor 3 may be in electronic communication with an imaging I/O 5. The imaging I/O 5 may be in electronic communication with an image capturing device 15, which can take an image of the delivery system 17 or any portion thereof. The image capturing device may include a charge coupled device, an ultrasonic sensor, and/or other image capturing devices. The charge coupled device may be configured to generate images such as x-ray images. The ultrasonic sensor may be configured to generate images based on reflected ultrasonic waves.

The processor 3 may be in electronic communication with a user interface 7. The user interface 7 may include a keyboard, mouse, and/or other user interfaces. The processor 3 may also be in electronic communication with a display 9. The display 9 may be configured to display images generated by the image capture device 15. In some embodiments, the imaging device 1 may print the images generated by the image capture device 15 using a printer or other device rather than or in addition to using a display 9.

Memory 11 may be in electronic communication with the processor 3. The memory 11 may include imaging device software 13. The imaging device software 13 may include instructions executable to perform portions of the functions described below.

Figure 2:
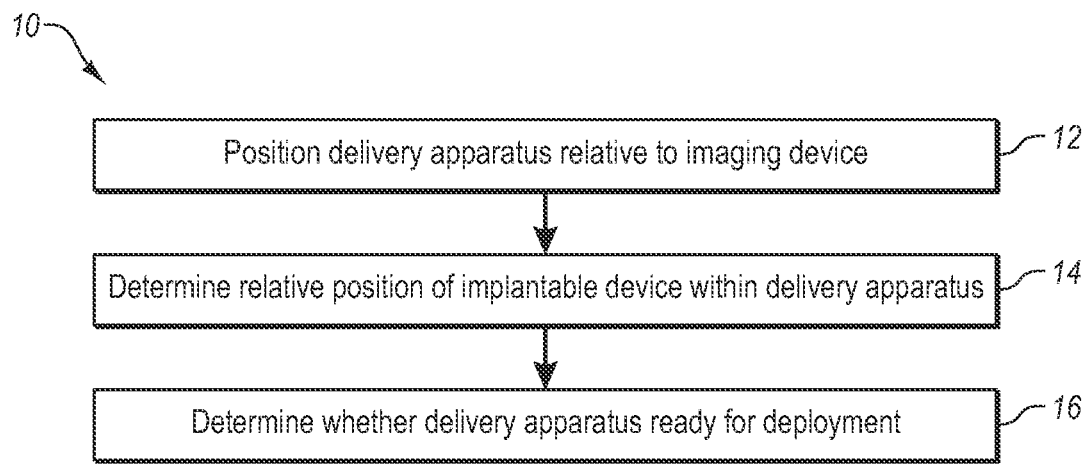
FIG. 2 illustrates an embodiment of a method for imaging a delivery system.

FIG. 2 illustrates an embodiment of a method 10 for imaging a delivery system. The method 10 may include positioning a delivery apparatus relative to an imaging device, as represented by block 12. In the present embodiment, the imaging device 1 shown in FIG. 1 may be used. For example, the delivery apparatus may be positioned relative to the image capture device 15. The imaging device 1 can then take an image of the delivery apparatus when activated.

Figure 20A:
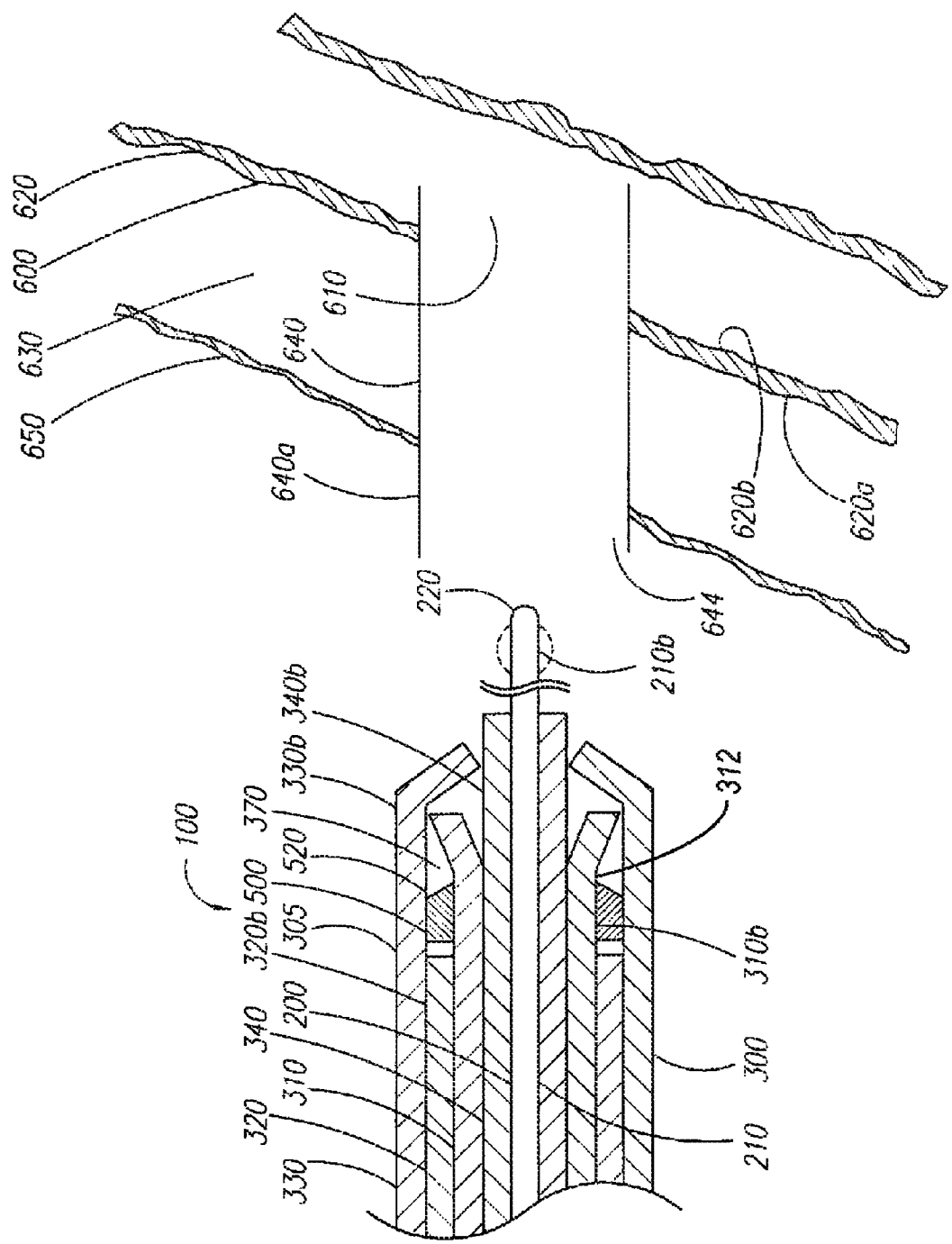
FIGS. 20A-20K illustrate various steps in the deployment of embodiments of the present invention.
Figure 20B:
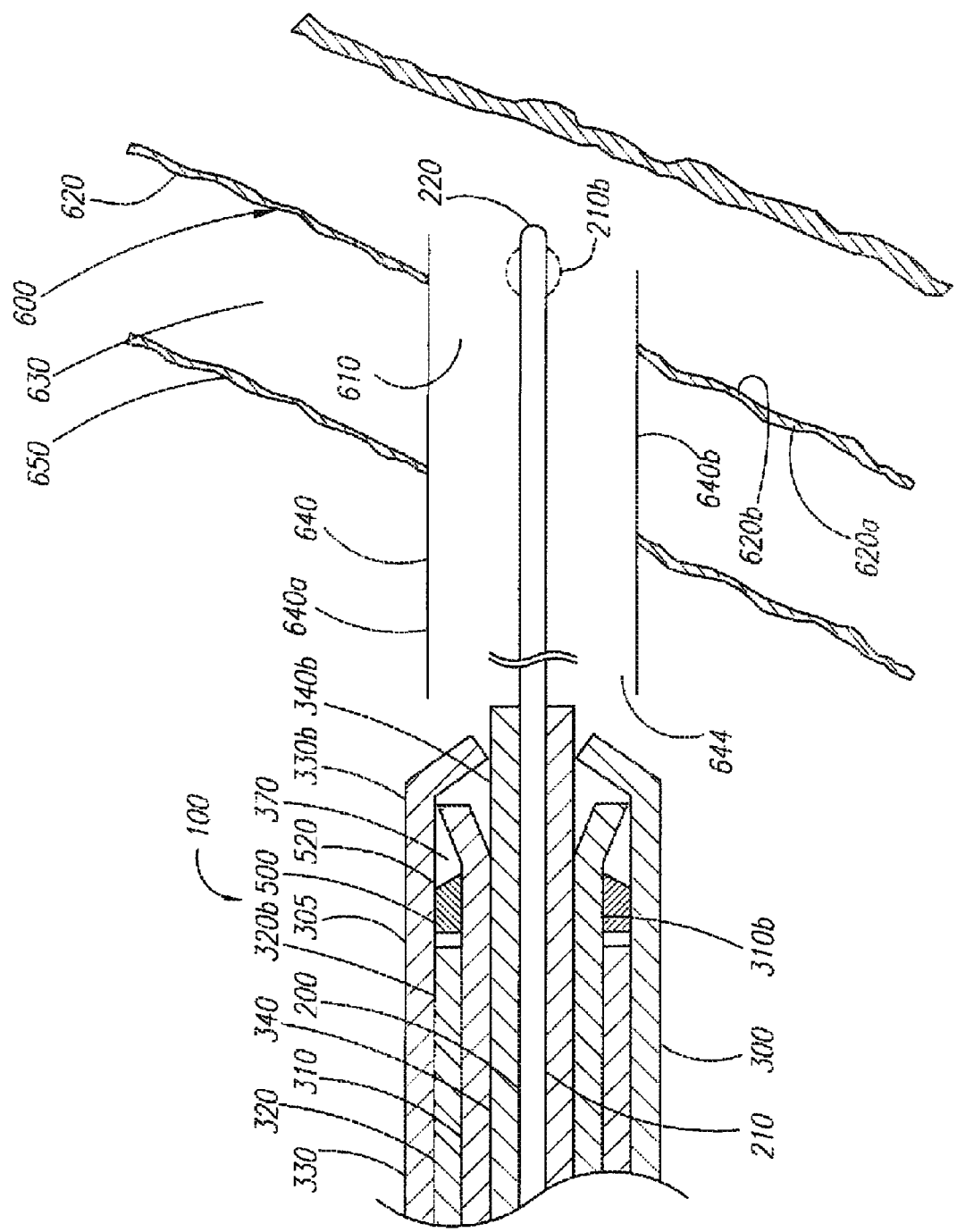
Figure 20C:
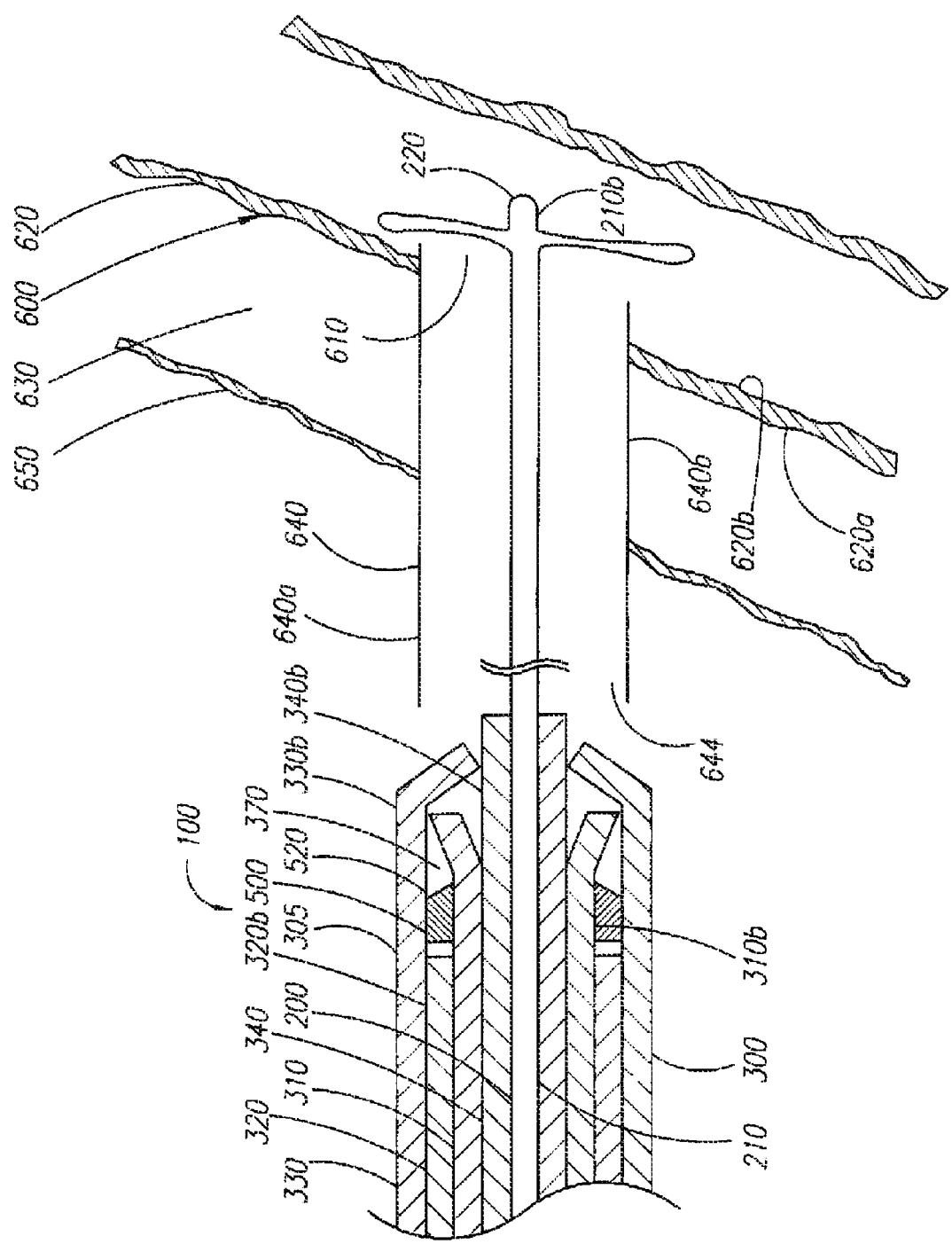
Figure 20D:
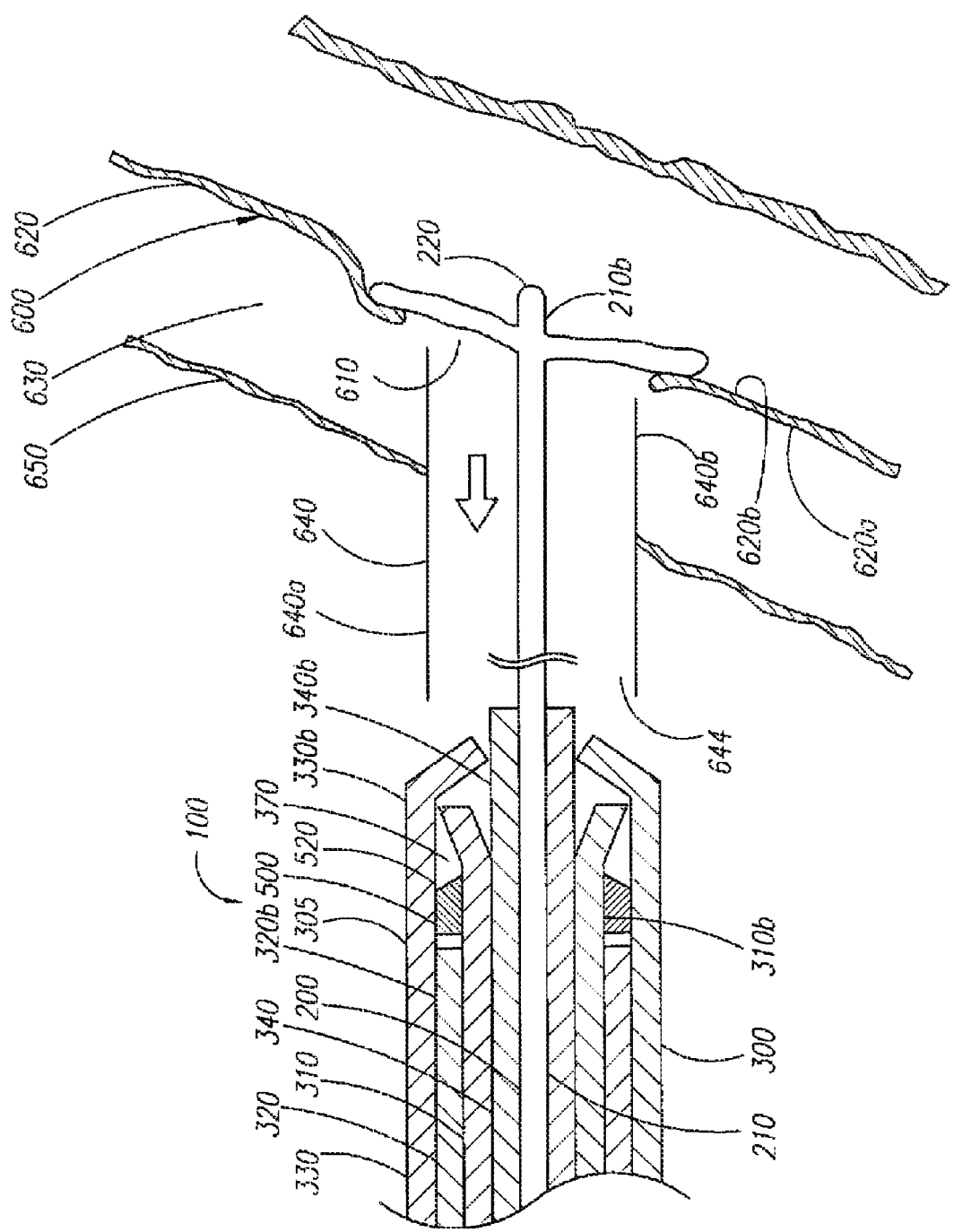
Figure 20E:
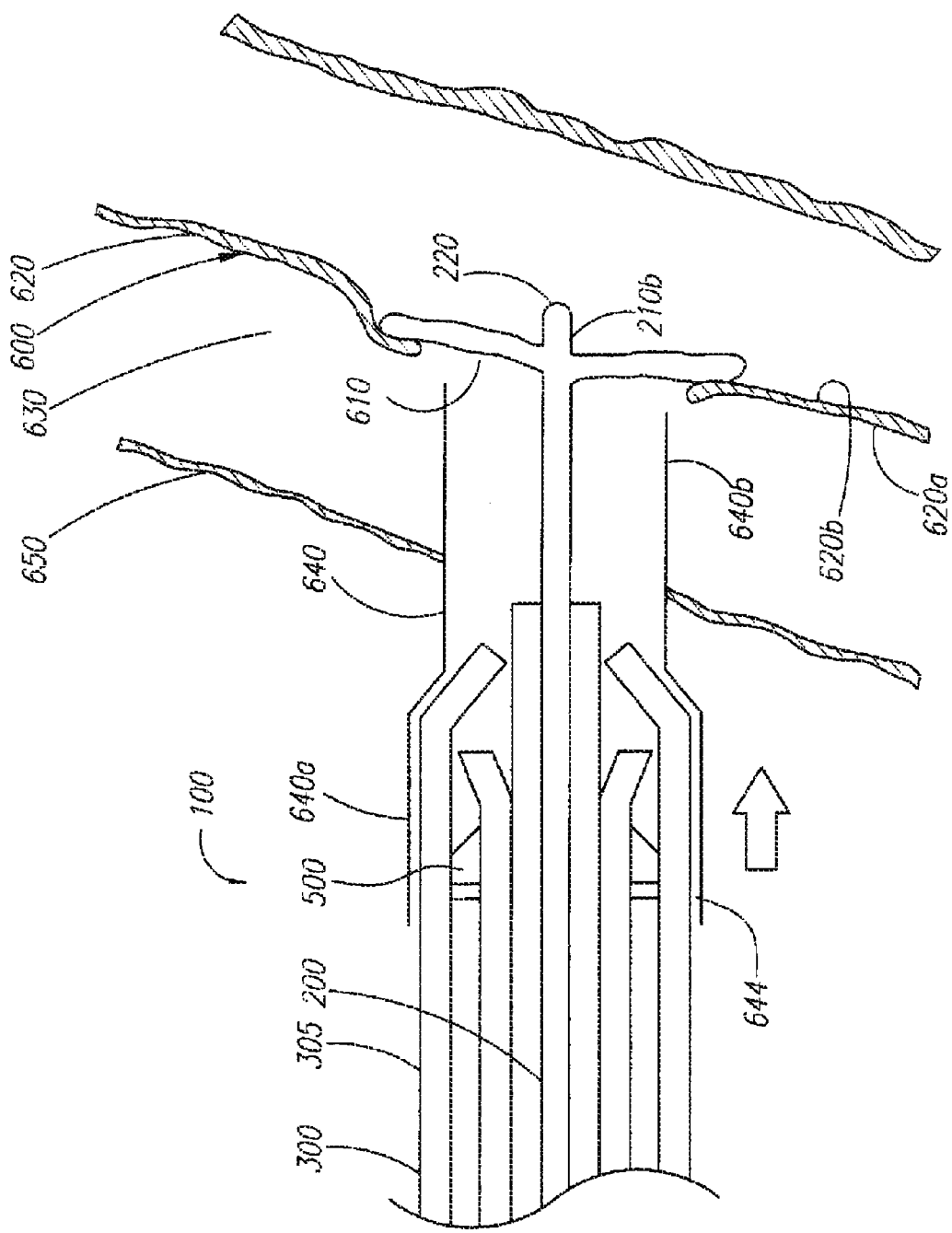
Figure 20F:
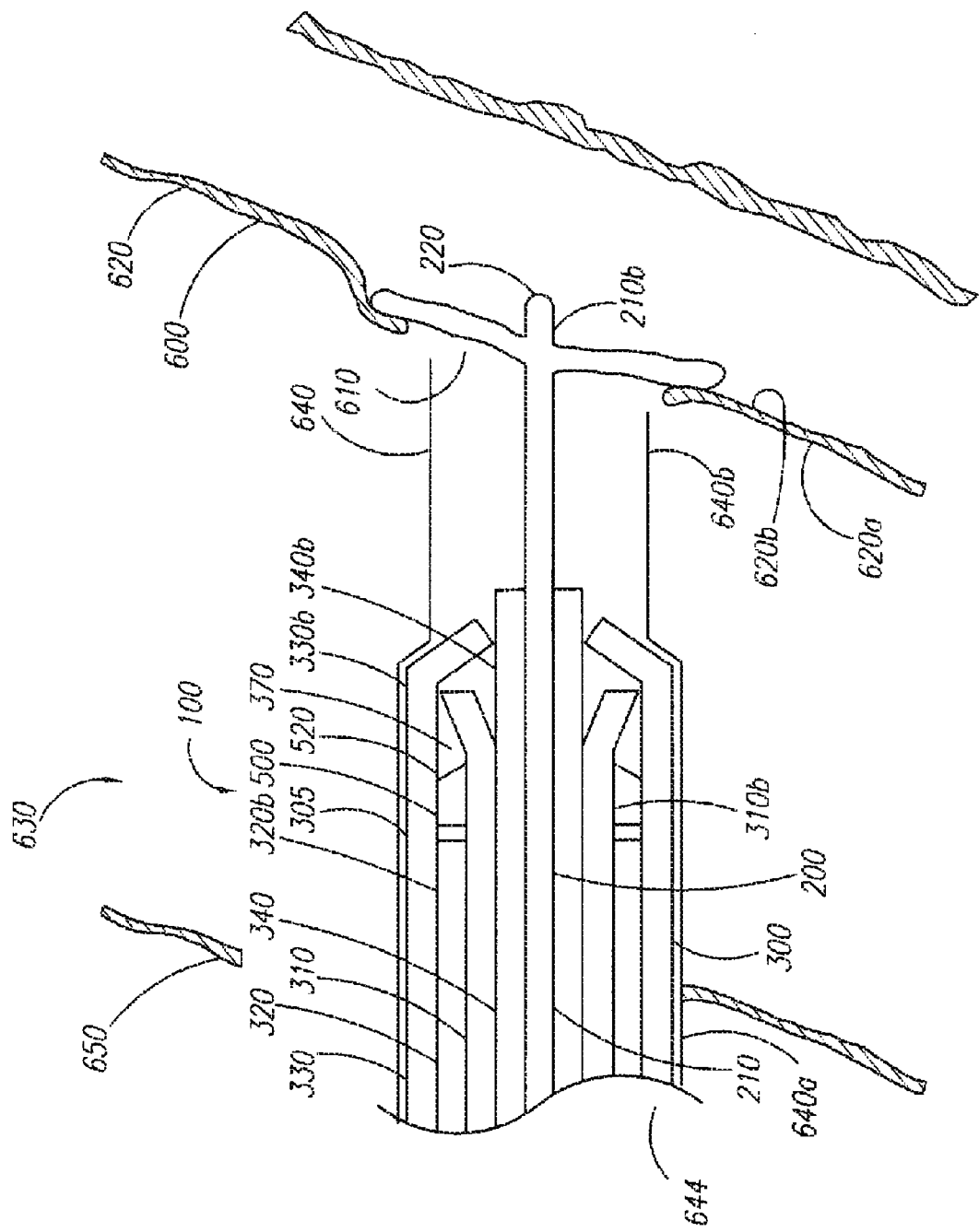
Figure 20G:
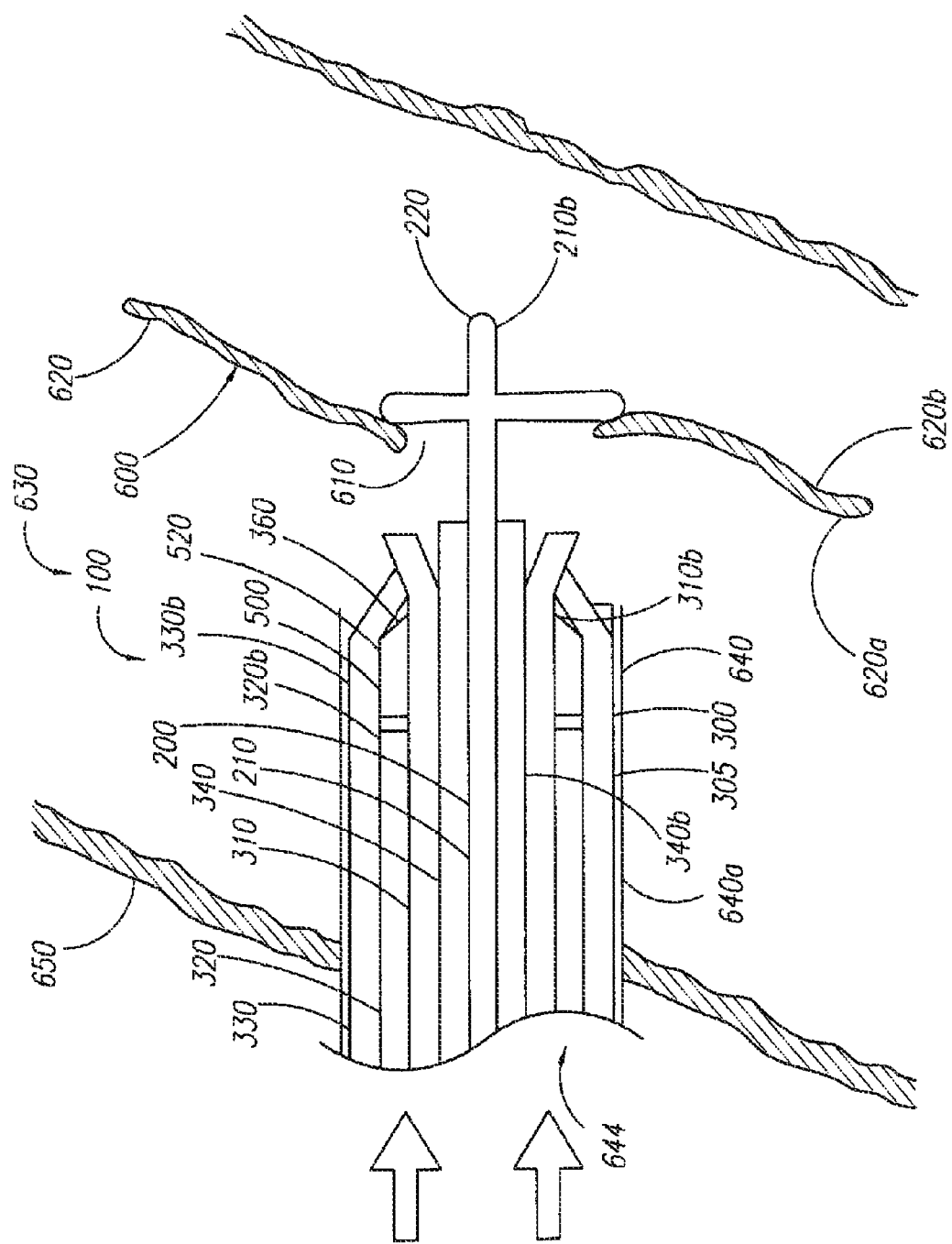
Figure 20H:
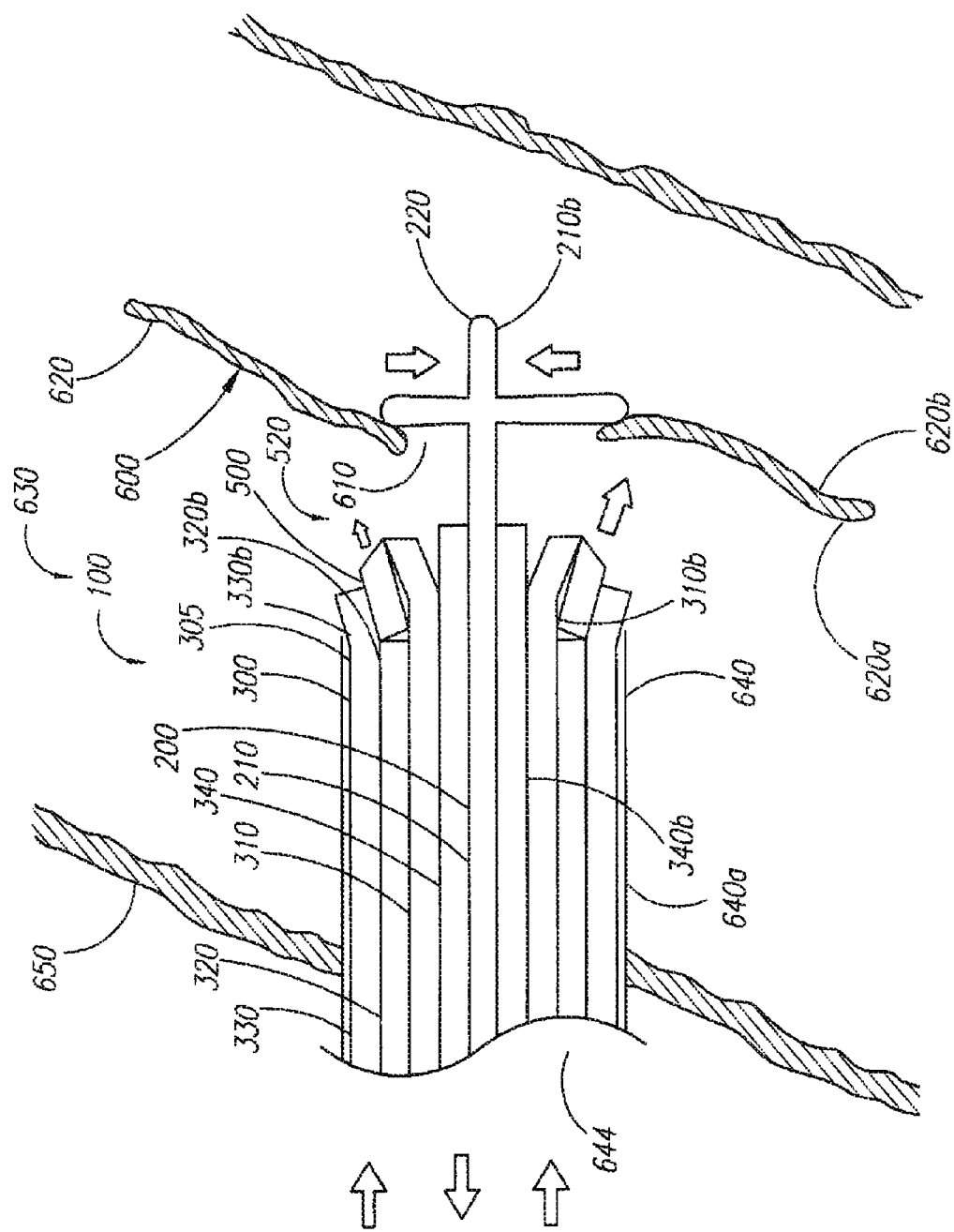
Figure 20I:
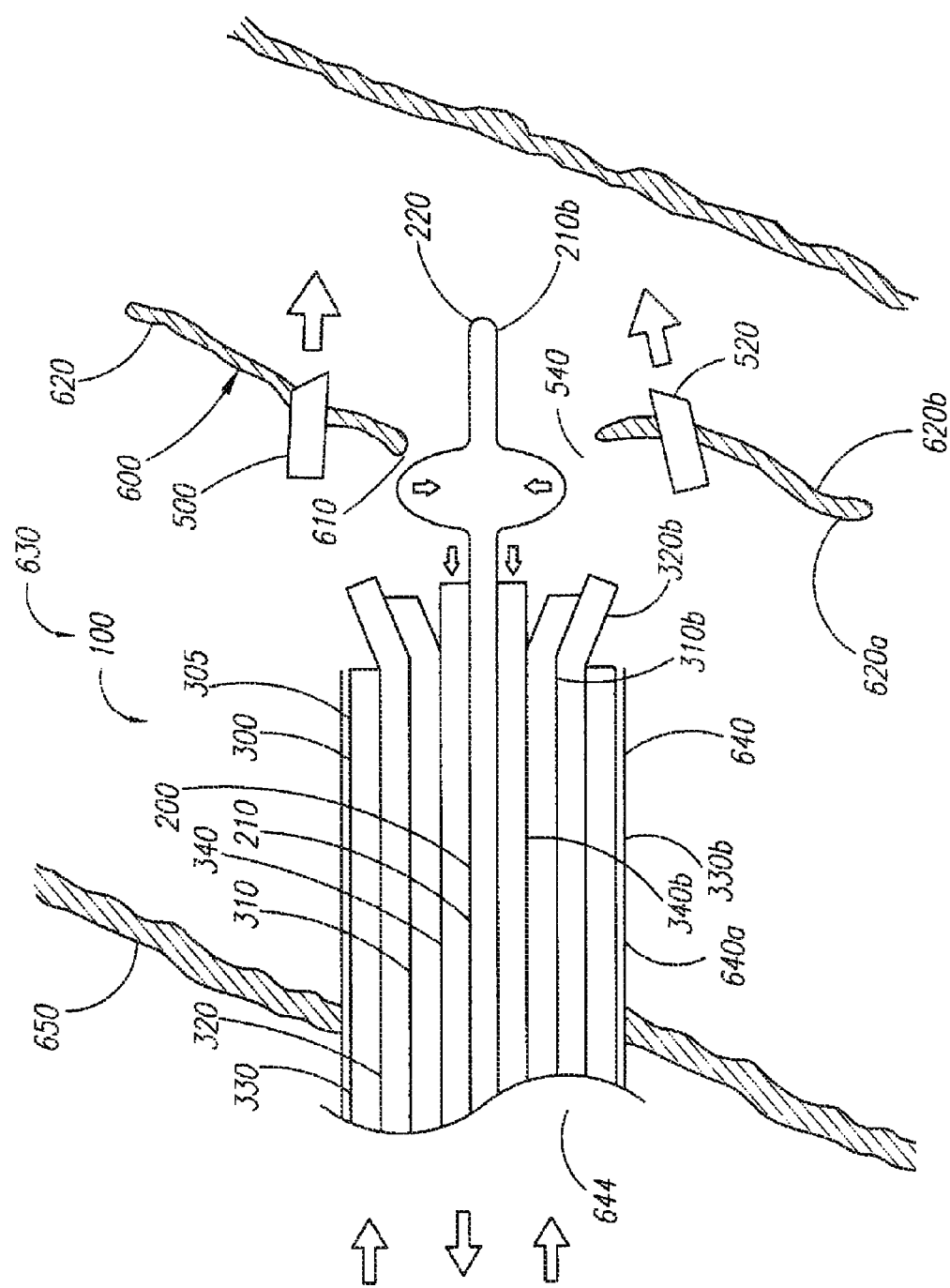
Figure 20J:
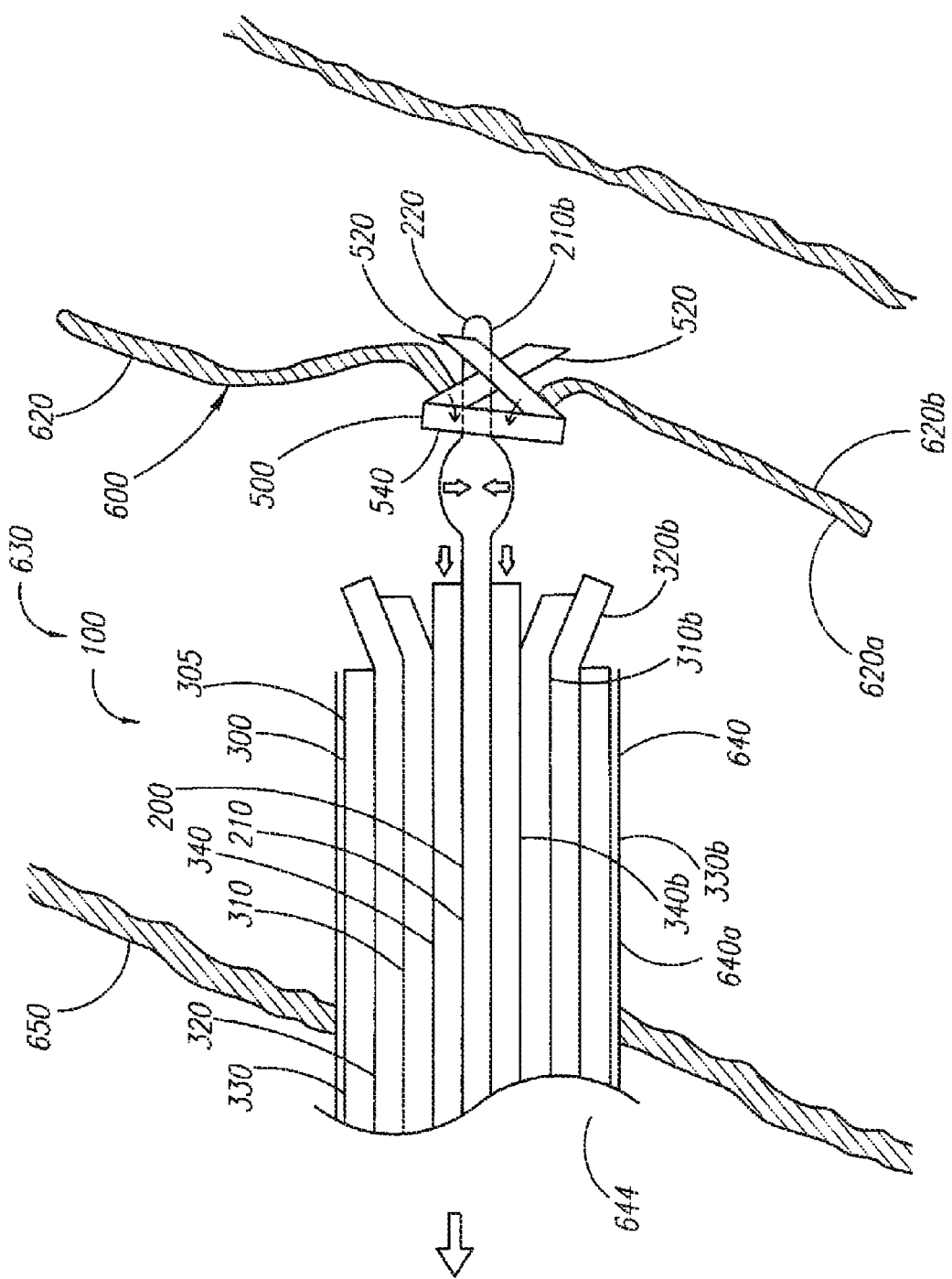
Figure 20K:
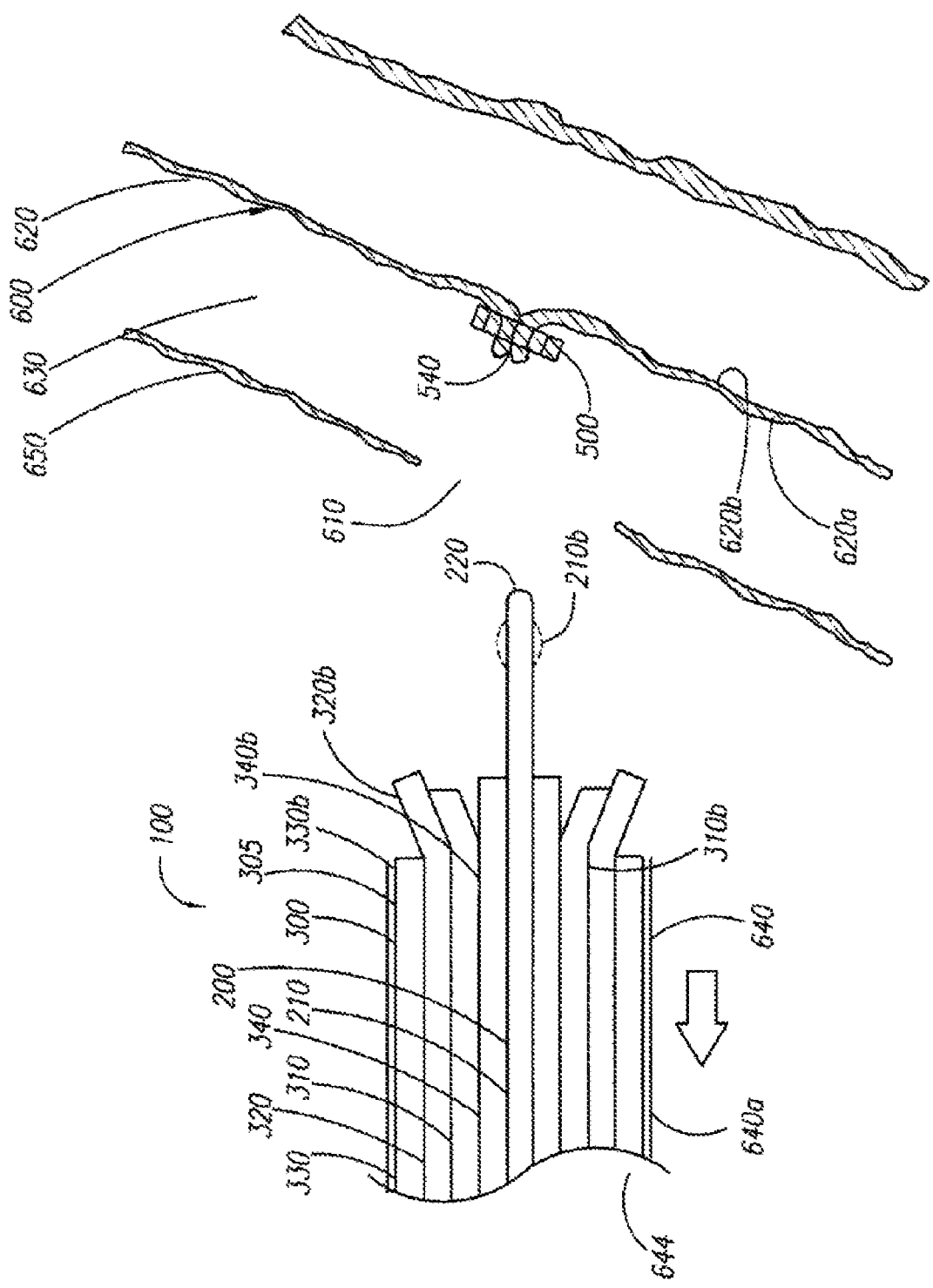
Figure 21:
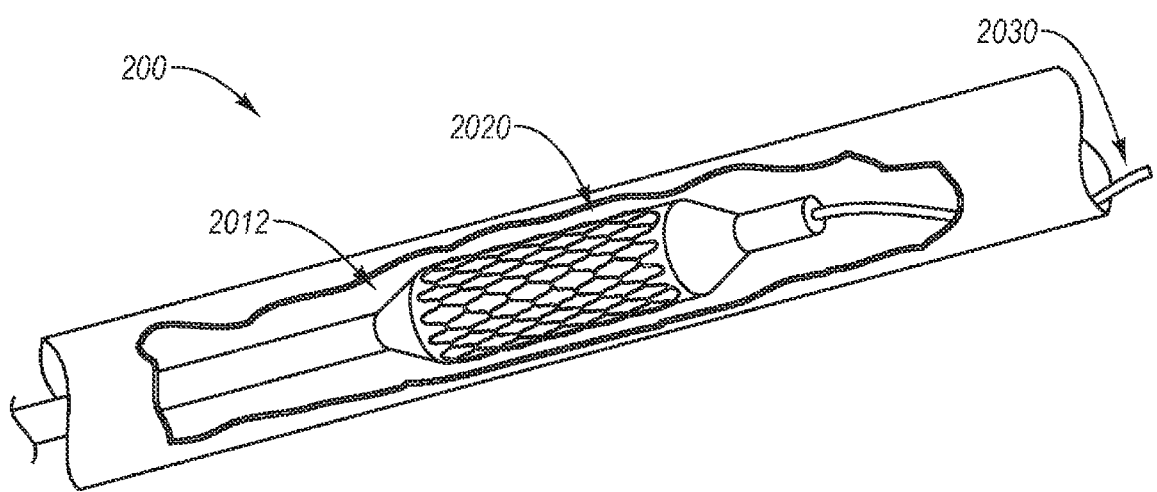
FIG. 21 illustrates a perspective view of an embodiment of a stent delivery apparatus.

A delivery apparatus may include a closure element delivery apparatus, like those shown in FIGS. 6A-18 and 20A-20K, a stent delivery apparatus, like the one shown in FIG. 21, or other delivery apparatus. Positioning the delivery apparatus relative to the imaging device may include placing the delivery apparatus in a fluoroscope and/or positioning an ultrasonic detector near the delivery apparatus. Other relative positions and/or imaging devices may also be used.

The relative position of an implantable device within the delivery apparatus may be determined, as represented by block 14. The implantable device may include a closure element, as shown in FIGS. 19A-19G, a stent, as shown in FIG. 21, and/or other implantable devices. The relative position of an implantable device may include the location within the delivery apparatus, the orientation within the delivery apparatus, and/or other aspects of the relative position relative to the delivery apparatus.

Determining the relative position of the implantable device within the delivery apparatus may be accomplished using the imaging device 1 as shown in FIG. 1. For example, the imaging device 1 may be a fluoroscope such that an x-ray image of the delivery apparatus and/or implantable device may be generated to visualize the relative position of the implantable device within the delivery apparatus.

It may be determined whether the delivery apparatus is ready for deployment, as represented by block 16. Determining whether the delivery apparatus is ready for deployment may include determining whether the implantable device is properly positioned within the delivery device and/or whether there may be some obstruction to proper deployment. Verification of proper positioning may help to prevent traumas to the patient caused by the removal of an improperly deployed implantable device or by the deployment of an improperly positioned implantable device.

Proper positioning may be predetermined. A proper position of an implantable device relative to a delivery apparatus may include a desired range of positions. For example, it may be desirable for an axis of an implantable device to be oriented with an axis of the delivery apparatus. A desired range of positions may include a range of acceptable orientations of the implantable device axis and the delivery apparatus axis, i.e. between 0 and 1 degrees of difference. It may also be desirable for the implantable device to be located in a predetermined location relative to the delivery apparatus. A desired range of positions may include a range of acceptable locations, i.e. distances from a point relative to the delivery apparatus, such as between 0 and 2 millimeters from the predetermined location. In the present embodiment, the implantable device may be generally positioned within the delivery apparatus. In other embodiments the implantable device may be generally positioned relative to the delivery apparatus (i.e. within or without). Further, the proper position of the implantable device may also depend on the stage of a procedure.

In the present embodiment, the relative position of the implantable device may be determined within the delivery apparatus before determining whether the delivery at apparatus is ready for deployment. In other embodiments, it may not be desirable to determine the relative position of the implantable device within the delivery apparatus before determining whether the delivery apparatus is ready for deployment.

Determining whether the delivery apparatus is ready for deployment may include determining whether there may be some obstruction to proper deployment. For example, at least one component of the delivery apparatus may be out of position, at least one component of the delivery apparatus may have a defect detectable by the imaging device, and/or some other obstruction to proper deployment may be detected. In further embodiments, it may be desirable to determine the relative position of the implantable device within the delivery apparatus and to determine whether there may be some obstruction to proper deployment before determining whether the delivery apparatus is ready for deployment. If it is determined that the delivery apparatus is ready for deployment, the delivery apparatus may be deemed acceptable for use.

Figure 3:
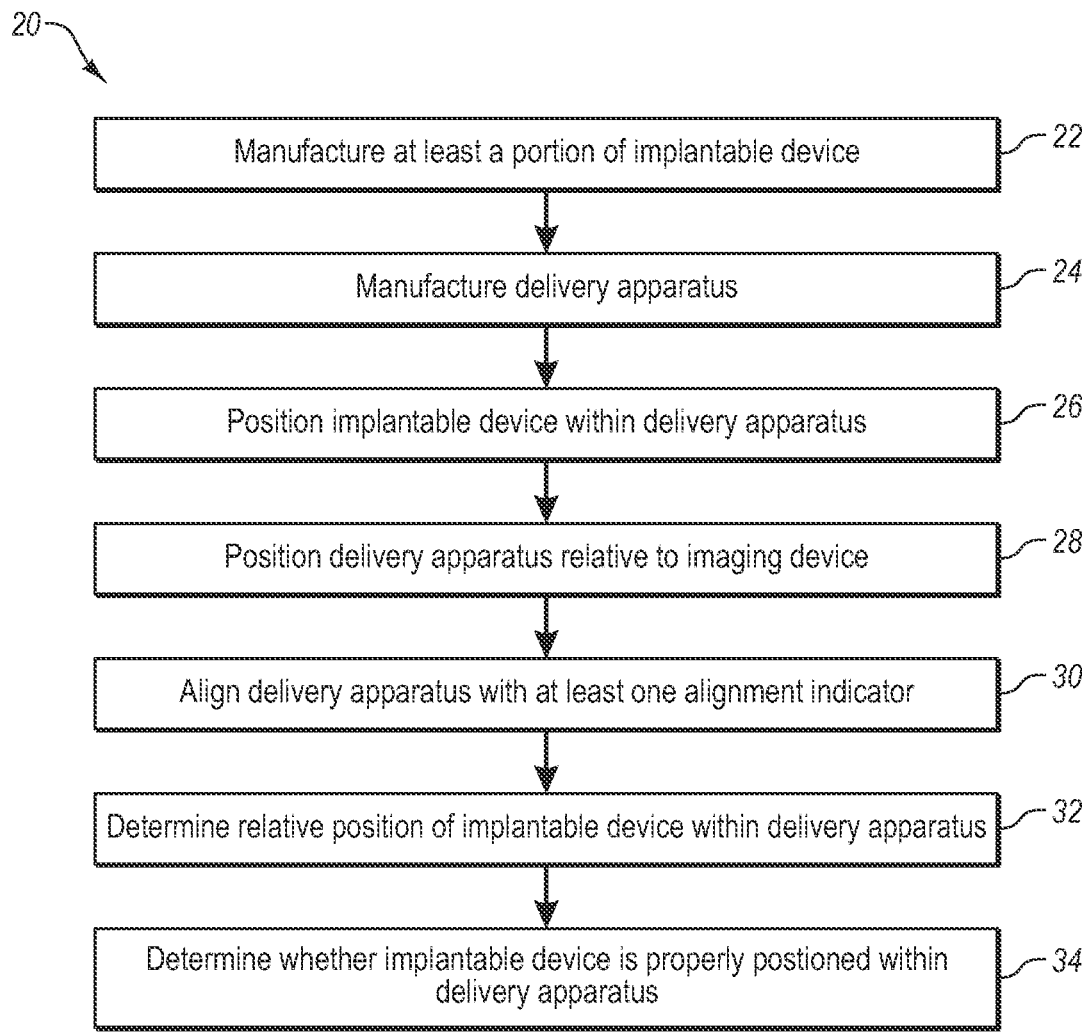
FIG. 3 illustrates another embodiment of a method for imaging a delivery system.

FIG. 3 illustrates another embodiment of a method 20 for imaging a delivery system. An implantable device may be manufactured, as represented by block 22. As discussed above, an implantable device may include a closure element, a stent, and/or other implantable devices. Manufacturing an implantable device may include forming and/or processing the implantable device.

Forming the implantable device may include forming tissue engaging portions (i.e. in the case of a closure element implantable device), support members (i.e. in the case of a stent implantable device and/or closure element implantable device), and/or other components of the implantable device. The implantable device may be formed from a base material. The base material may be a shape memory material, such as alloys at of nickel-titanium, and/or other materials.

Processing the implantable device may include providing the base material. The base material may include a mixture. For example, the base material may contain more than one material within the mixture. Processing the implantable device may include coating at least a portion of the base material with a coating.

The delivery apparatus may be manufactured, as represented by block 24. As discussed above, a delivery apparatus may include a closure element delivery apparatus, a stent delivery apparatus, and/or other delivery apparatus. Manufacturing a delivery apparatus may include forming and/or processing the delivery apparatus.

Forming the delivery apparatus may include forming various components of the delivery apparatus. For example, in embodiments where a closure element delivery apparatus may be used, the delivery apparatus may include a locator assembly, a carrier assembly, and/or other delivery apparatus components. The delivery apparatus may be formed from a base material. As with the base material of the implantable device, the base material of the delivery apparatus may be a shape memory material, such as alloys of nickel-titanium and/or other materials.

Processing the delivery apparatus may include providing the base material for at least one delivery apparatus component. The base material may include a mixture. Processing the delivery apparatus may include coating at least a portion of at least one component of the delivery apparatus with a coating. A delivery apparatus may have a base material including a mixture and/or may be coated with a material.

The base materials and/or coatings used with the implantable device and/or delivery apparatus may include a material that may make the implantable device and/or delivery apparatus capable of being viewed by an imaging device, such as imaging device 1 as shown in FIG. 1. Materials that may make the implantable device and/or delivery apparatus capable of being viewed by an imaging device may include radiopaque materials and/or dense materials (i.e. materials capable of being viewed by an ultrasonic imaging device), which may include high density materials such as gold, platinum, platinum/iridium, and/or other radiopaque materials. As used herein, the term radiopaque may include partial radiopacity as well as total radiopacity. These materials can be part of the base material from which the delivery apparatus and/or implantable device are formed or can be included as part of the coatings discussed herein.

Other materials that may make the implantable device and/or delivery apparatus capable of being viewed by an imaging device may include dense materials. For example, if the imaging device uses ultrasonic waves to generate images, components of the delivery apparatus and/or implantable device that are denser may reflect more ultrasonic waves than those that are less dense.

The implantable device may be positioned within the delivery apparatus, as represented by block 26. For example, a closure element or stent may be positioned within a closure element delivery apparatus or stent delivery apparatus, respectively. Positioning an implantable device within a delivery apparatus will be further discussed below.

The delivery apparatus may be positioned relative to the imaging device, as represented by block 28. In the present embodiment, the imaging device 1 shown in FIG. 1 may be used. Positioning the delivery apparatus relative to the imaging device may include placing the delivery apparatus in a fluoroscope and/or positioning an at ultrasonic detector near the delivery apparatus. Other relative positions and/or imaging devices may also be used. In the present embodiment, a user may position the delivery apparatus relative to the imaging device. In other embodiments, the imaging device may include a positioning feature that may automatically position the delivery apparatus.

The delivery apparatus may be aligned with at least one alignment indicator, as represented by block 30. For example, a fixture, such as a jig, may be used to position the delivery apparatus relative to the imaging device. The fixture may include alignment indicators to facilitate accelerated positioning of the delivery apparatus. In some embodiments, the fixture may have physical boundaries, such as a cavity shaped to receive the delivery apparatus. In other embodiments, a fixture may be less desirable and simple indicators to position the delivery apparatus relative to the imaging device may be used.

The relative position of the implantable device within the delivery apparatus may be determined, as represented by block 32. Determining the relative position of the implantable device within the delivery apparatus may be accomplished using the imaging device 1. For example, the imaging device may be a fluoroscope such that an x-ray image of the delivery apparatus and/or implantable device may be generated to visualize the relative position of the implantable device within the delivery apparatus.

It may be determined whether the implantable device is properly positioned within the delivery apparatus, as represented by block 34. As discussed above, proper positioning may be predetermined and the image can be used to determine whether the implantable device is within tolerance of the predetermined proper positioning. If it is determined that the implantable device is properly positioned within the delivery apparatus, the delivery apparatus may be deemed acceptable for use. If it is determined that the implantable device is not properly positioned within the delivery apparatus, the delivery apparatus may be deemed unacceptable for use. In other embodiments, if it is determined that the implantable device is not properly positioned within the delivery apparatus, the implantable device may be moved within the delivery apparatus and the method 20 may continue by positioning the delivery apparatus relative to the imaging device. Proper positioning may be based on empirical data regarding past proper and/or improper deployments of the implantable device.

Figure 4:
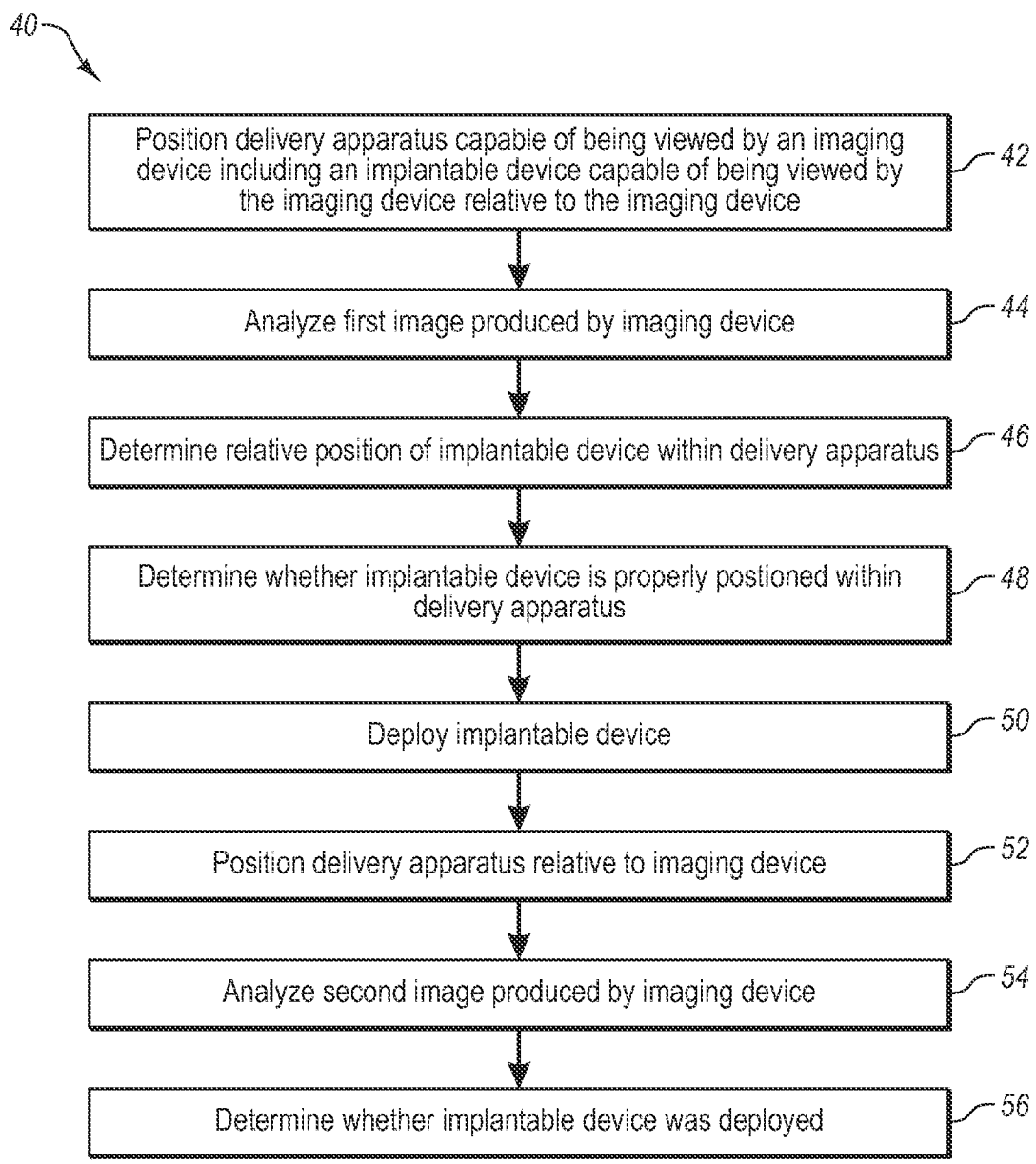
FIG. 4 illustrates an embodiment of a method for determining whether an implantable device has deployed.

FIG. 4 illustrates an embodiment of a method 40 for determining whether an implantable device has deployed. The delivery apparatus may be positioned relative to the imaging device, as represented by block 42. In the present embodiment, the delivery apparatus and/or implantable device may be capable of being viewed by an imaging device. Being capable of being viewed by an imaging device may include having a portion of the delivery apparatus and/or implantable device that is, for example, radiopaque. Positioning the delivery apparatus relative to the imaging device may include placing the delivery apparatus in a fluoroscope and/or positioning an ultrasonic detector near the delivery apparatus. Other relative positions and/or imaging devices may also be used.

An image may be produced by the imaging device. In the present embodiment, producing an image may include generating the image on a display, such as the display 9 of the imaging device 1 shown in FIG. 1. In other embodiments, producing an image may include printing or otherwise reproducing an image. In further embodiments, the image may be stored in the memory 11 of the imaging device 1. In some embodiments, the image produced may be a partial image. For example, the image may include only a distal end of the delivery apparatus. In another example, the image may include a view of the entire delivery apparatus.

The image may be analyzed, as represented by block 44. Analyzing the image may include comparing the generated image to a previously generated image. In the present embodiment, analyzing the image may be performed by a user and/or other technician. In other embodiments, the image may be automatically analyzed by the imaging device. Analysis of the image may allow for an unobtrusive diagnosis of a past, present, and/or potential problem with the proper deployment of the implantable device. The relative position of the implantable device within the delivery device may be determined, as represented by block 46. Determining the relative position of the implantable device within the delivery apparatus may be accomplished using the imaging device 1, as described above.

It may be determined whether the implantable device is properly positioned within the delivery apparatus, as represented by block 48. As discussed above, proper positioning may be predetermined. The determination whether the implantable device is properly positioned within the delivery apparatus may be made by comparing the generated image to a previously generated image and an acceptable range of predetermined values. For example, a predetermined range of acceptable variances from a desired position (i.e. location, orientation, and/or other position) may be used to determine whether the implantable device is properly positioned within the delivery apparatus. In the present embodiment, the user may make this determination. In other embodiments, this determination may be made automatically, for example by the imaging device 1.

If it is determined that the implantable device is properly positioned within the delivery apparatus, the implantable device may be deployed, as represented by block 50. Deploying an implantable device is discussed in more detail below. If it is determined that the implantable device is not properly positioned within the delivery apparatus, the delivery apparatus may be deemed unacceptable for use and/or the method 40 may end.

After an attempt to deploy the implantable device is made, the delivery apparatus may be positioned relative to the imaging device, as represented by block 52. Positioning the delivery apparatus relative to the imaging device may be performed as described above.

A second image may be produced by the imaging device. For example, as described above, the second image may be generated on a display. The second image may be analyzed, as represented by block 54. For example, the current (second) image may be analyzed by comparing the generated image to the image generated prior to the deployment attempt.

It may be determined whether the implantable device was deployed, as represented by block 56. This determination may be made by comparing the position of the implantable device in the first image to the position of the implantable device second image. For example, if the implantable device does not appear in the second image, it may be determined that the implantable device was deployed. This determination, like other determinations described, may be performed by a user and/or may be performed automatically by the imaging device.

Figure 5:
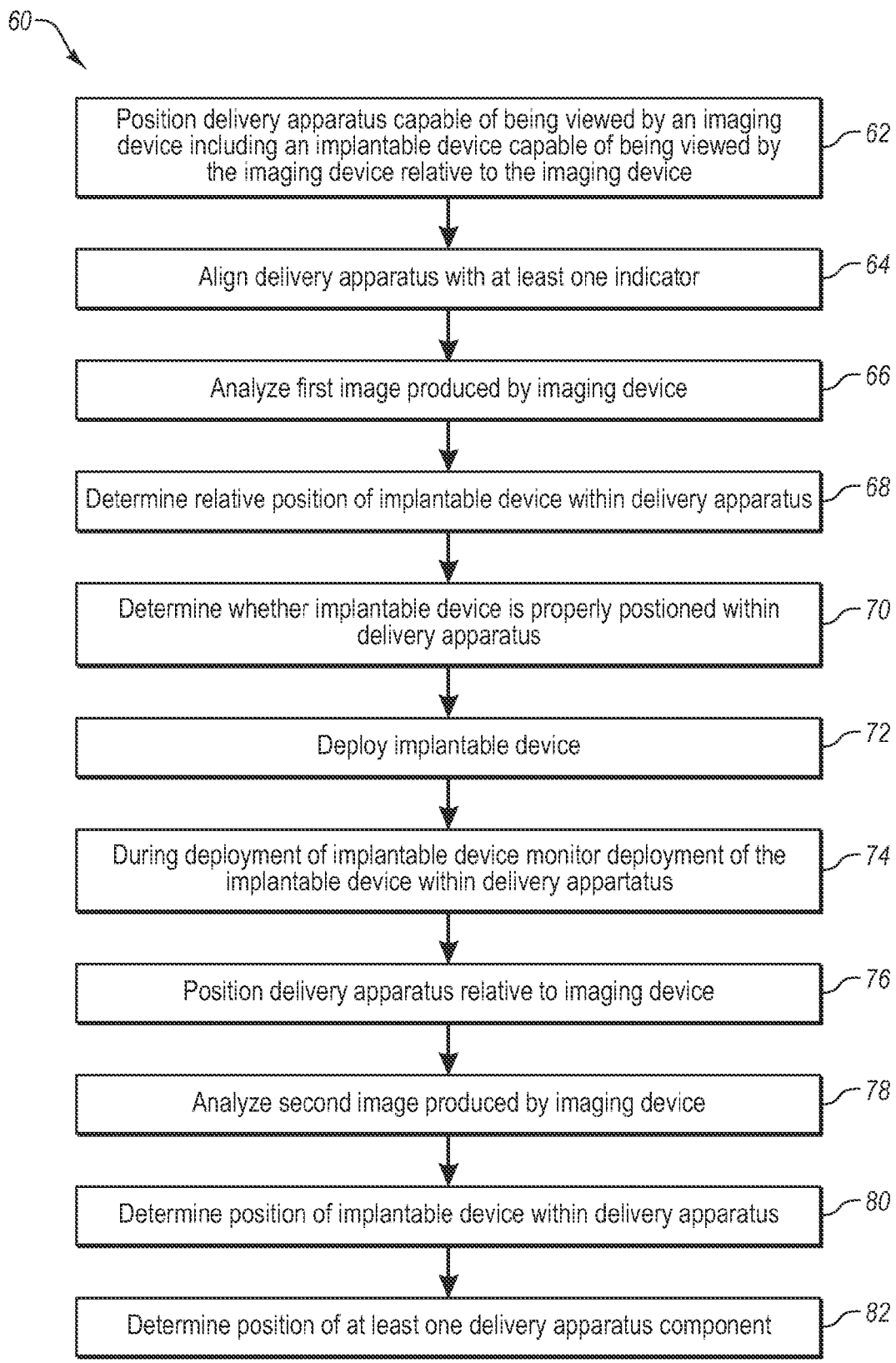
FIG. 5 illustrates a further embodiment of a method for imaging a delivery system.

FIG. 5 illustrates a further embodiment of a method 60 for imaging a delivery system. The delivery apparatus may be positioned relative to the imaging device, as represented by block 62. In the present embodiment, the delivery apparatus and/or implantable device may be capable of being viewed by an imaging device, as described above.

The delivery apparatus may be aligned with at least one alignment indicator, as represented by block 64. The alignment indicators may facilitate accelerated positioning of the delivery apparatus, as described above.

An image may be produced by the imaging device. In the present embodiment, producing an image may include generating the image on a display, such as the display 9 of the imaging device 1 shown in FIG. 1. In other embodiments, producing an image may include printing and/or otherwise reproducing an image.

The image may be analyzed, as represented by block 66. Analyzing the image may include comparing the generated image to a previously generated image, as described above. Analyzing the image may also include a computer driven analysis of the image that searches for indications of the presence of an implantable device within a particular area. Thus, the presence and/or proper positioning of an implantable device within a delivery apparatus can be determined by an analysis of the generated image.

The relative position of the implantable device may be determined within the delivery device, as represented by block 68. Determining the relative position of the implantable device within the delivery apparatus may be accomplished using the imaging device 1, as described above.

It may be determined whether the implantable device is properly positioned within the delivery apparatus, as represented by block 70. As discussed above, proper positioning may be predetermined. Thus, the implantable device should be located at a particular location within the delivery apparatus prior to deployment, for example. The determination whether the implantable device is properly positioned within the delivery apparatus may be made by comparing the generated image to a previously generated image and an acceptable range of predetermined values, as described above. Alternatively, the generated image itself can be used. For example, the resulting image may have different associated values (e.g., pixel or color values in a certain region of the image) that reflect the presence or absence of an implantable device. This can be attributed to the different densities associated with the presence or absence of the implantable device.

In the present embodiment, if it is determined that the implantable device is properly positioned within the delivery apparatus, the implantable device may be deployed, as represented by block 72. Deploying an implantable device is discussed in more detail below. In other embodiments, the implantable device may be deployed regardless of the position of the implantable device within the delivery apparatus. For example, it may be desirable to determine the effects of deploying an out-of-position implantable device.

The deployment of the implantable device may be monitored, as represented by block 74. The deployment of the implantable device may be monitored before, during, and/or after deployment.

Monitoring the deployment of the implantable device may include monitoring the implantable device within the delivery apparatus and/or outside of the delivery apparatus. Furthermore, monitoring the deployment of the implantable device may include monitoring components of the delivery apparatus before, during, and/or after deployment of the implantable device.

The deployment of the implantable device may be monitored using an imaging device. For example, the implantable device may be deployed while within the imaging device. Additionally, multiple imaging devices may be used to monitor various portions of the delivery apparatus. For example, interactions between various components of the delivery apparatus may be monitored as they interact with the implantable device.

Monitoring the deployment of the implantable device may include monitoring the location, orientation, acceleration, velocity, size, shape, and/or other aspects of the deployment. For example, a trajectory of the implantable device may be generated from information obtained by monitoring the deployment of the implantable device.

The delivery apparatus may be positioned relative to the imaging device 76. In the present embodiment, the delivery apparatus may be positioned relative to the imaging device after the implantable device has been deployed, as described above. Positioning the delivery apparatus may include aligning the delivery apparatus with at least one alignment indicator, as described above.

An image may be produced by the imaging device, as described above. The image may be analyzed, as represented by block 78. Analyzing the image may include comparing the generated image to a previously generated image, as described above. By analyzing the image of the delivery apparatus, the user and/or imaging device typically may look inside the delivery apparatus without disassembling the delivery apparatus.

In cases where the implantable device did not deploy, the cause of the failed deployment may be determined. Determining the cause of a failed deployment may include determining the relative position of the implantable device within the delivery device, as represented by block 80. Determining the relative position of the implantable device within the delivery apparatus may be accomplished using the imaging device 1, as described above.

Determining the cause of a failed deployment may include determining the relative position of at least one delivery apparatus component, as represented by block 82. In the present embodiment, this determination may be made in cases where the implantable device did not deploy. In other embodiments, the relative position of at least one delivery apparatus component may be determined regardless of a successful deployment.

Determining the cause of a failed deployment may include determining whether an obstruction to deployment exists and/or existed. For example, an interaction between the components of the delivery apparatus may have contributed to and/or caused the failure.

Determining the cause of a failure may facilitate a determination whether it may be likely that a failure was due to a manufacturing defect and/or customer misuse. Once the source of the problem is properly identified, the cause of failed deployment may more readily be addressed.

Furthermore, determining the position of the implantable device within the delivery apparatus and/or determining the position of at least one delivery apparatus component may facilitate a behavioral diagnostic of the delivery apparatus. For example, the various determinations may be useful for research and development of improvements in the deployment fidelity of the implantable device and/or other improvements to the delivery apparatus. It may be useful to observe how an experimental change to the delivery apparatus may affect the deployment behavior of the delivery apparatus and/or implantable device. Thus, the present embodiment may facilitate determination of the effects of a design change to the delivery apparatus and/or to one or more constitutive parts of the delivery apparatus on the overall behavior of the delivery apparatus.

Using an imaging device may include several advantages over disassembling the delivery apparatus to perform a diagnosis. For example, the cause of a failure of the delivery apparatus may be from a portion of the delivery apparatus that may be destroyed and/or otherwise compromised by taking apart the delivery apparatus. Destruction and/or compromise of diagnostically relevant information during the disassembly process of the delivery apparatus may be avoided by using an imaging device. The use of an imaging device may not be as labor intensive as a manual disassembly of the delivery apparatus. For example, use of an imaging device may facilitate more quick and efficient diagnoses. In some embodiments, careful disassembly of the delivery apparatus may not be required. For example, the delivery apparatus may only need to be placed into the imaging device and the resulting image analyzed.

In order to facilitate the proper diagnosis of a failure and/or defect of a delivery apparatus, a plurality of constituent components may include material capable of being viewed by an imaging device. In some embodiments, the material may vary in the capability of being viewed by the imaging device. For example a plurality of constituent components may be constructed of materials with varying degrees of radiopacity and/or density. Using materials differing in the capability of being viewed by an imaging device may enable the analyzing technician to more quickly identify the potential causes of a failure and/or defect of a delivery apparatus. For example, using materials of varying radiopacity and/or density may make it easier for the technician to separate and/or identify the different components of the delivery apparatus and/or implantable device as represented on the image produced by the imaging device.

Portions of the delivery apparatus and/or implantable device may be partially coated with material by using masking techniques. For example, the entire implantable device and/or a component of the delivery apparatus may first be coated with material capable of being viewed by an imaging device. The implantable device and/or delivery apparatus may then be masked at locations where the material capable of being viewed by an imaging device coating may be desired. For example, a portion of the implantable device may be left unmasked during this process if it is desired to leave that portion uncoated. This may be desirable, e.g., to prevent the material from adversely affecting the flexibility of the implantable device. The implantable device may then be treated to remove the material capable of being viewed by an imaging device from the unmasked areas. The masking may then be removed using conventional processes, leaving the rest of the implantable device coated with material capable of being viewed by an imaging device.

In another alternative, one or more discrete markers may be provided at predetermined locations on the implantable device and/or portions of the delivery apparatus. For example, high density or radiopaque material may be crimped or otherwise secured onto portions of the implantable device and/or the delivery apparatus. In another embodiment, a plurality of pockets may be provided on the implantable device and/or the delivery apparatus into which high density plugs (not shown) may be bonded or otherwise secured. These various markers may also be incorporated in any of the embodiments described herein.

The following is a detailed description of embodiments of delivery apparatus. FIGS. 6A-18 and 20A-20K generally illustrate embodiments of a closure element delivery apparatus. FIG. 21 illustrates an embodiment of a stent delivery apparatus. Likewise examples of proper interactions and/or positioning between the various components of the delivery apparatus are generally described. It will be appreciated that other configurations of the components of a delivery apparatus may be used in conjunction with the present invention. Although some interactions may be highlighted in the following description, other disclosed and/or not disclosed configurations and/or interactions may be used. Furthermore, some components of the delivery apparatus and/or implantable devices may be described as including material capable of being viewed using an imaging device incorporated into at least a portion of a coating over and/or a mixture with the material of the indicated components and/or implantable devices. However, other components of the delivery apparatus and/or implantable devices may include material capable of being viewed using an imaging device incorporated into at least a portion of a coating over and/or a mixture with the material of the delivery apparatus components and/or implantable devices.

Figure 6A:
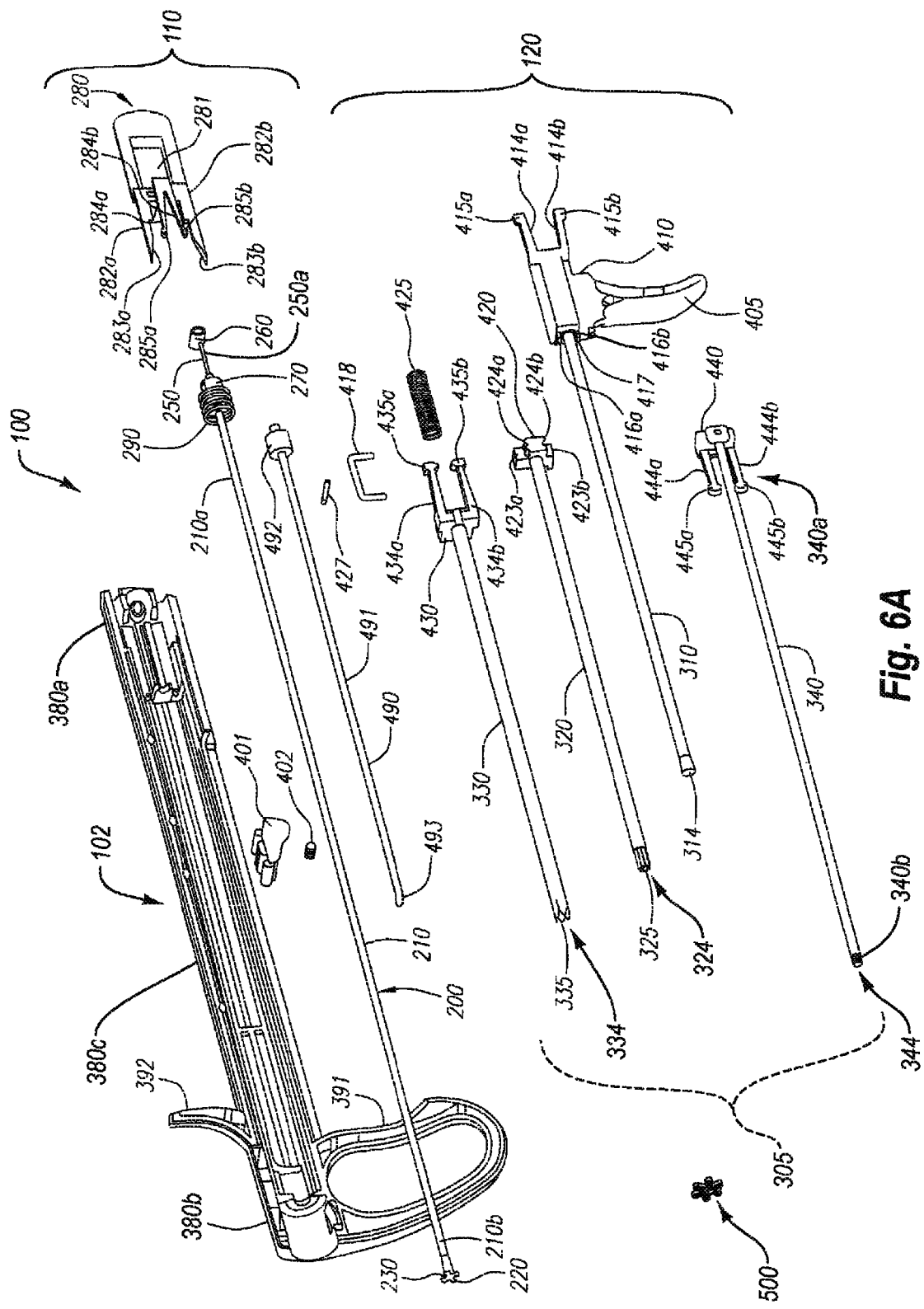
FIG. 6A illustrates an assembly view of the components of one embodiment according to the present invention for closing openings in tissue.
Figure 6B:
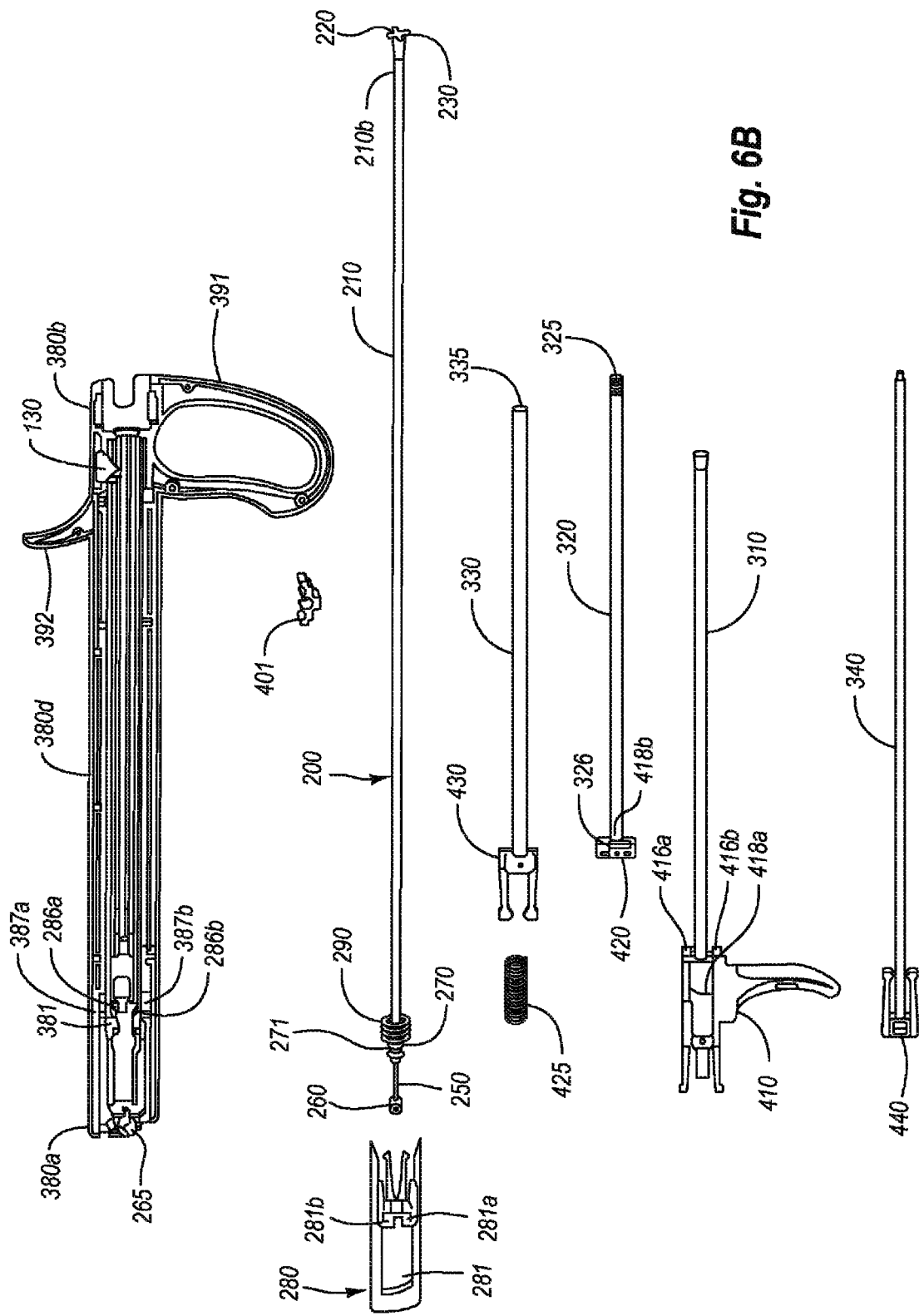
FIG. 6B illustrates another assembly view of the components of one embodiment according to the present invention for closing openings in tissue.

Referring now to FIGS. 6A-6B, an exploded assembly view of one delivery apparatus is shown in accordance with the present invention. As shown in FIGS. 6A-6B, the apparatus can include a housing that receives or retains a plurality of tubular members. The tubular members can be concentrically disposed within the housing of the device, with each tubular member having an associated block member fixedly attached to the proximal end thereof. The block members can be configured to interact with each other as well as with features of the housing, such as through movement of a triggering system. The interaction of the tubular members, the blocks, and the triggering system will be described in greater detail below. Also described below will be additional details regarding the handle portion of the housing and the manner by which the movement of the tubular members and the triggering system results in variation of the devices operational configuration to accommodate for physician or clinician hand sizes.

With continued reference to FIGS. 6A and 6B, apparatus 100 can be provided as one or more integrated components and/or discrete components that may be retained within a housing 102, having a housing top half 380c and a housing bottom half 380d. For example, apparatus 100 can include a locator assembly 110 and a carrier assembly 120. For purposes of illustration, locator assembly 110 and carrier assembly 120 are shown in FIG. 6A as having substantially separate assemblies. As desired, however, locator assembly 110 and carrier assembly 120 each can be provided, in whole or in part, as one or more integrated assemblies.

Turning to FIGS. 6A-7, 9, and 11, the assembly 110 can include a locator assembly 200. This locator assembly 200 can include flexible or semi-rigid tubular body 210 (such as an elongate rail) with a longitudinal axis. Tubular body 210 can have a proximal end region 210a and a distal end region 210b and can include a predetermined length and a predetermined outer cross-section, both of which can be of any suitable dimension. Distal end region 210b of locator assembly 200, as shown in more detail in FIGS. 8B and 8C, can include a substantially rounded, soft, and/or flexible distal end or tip 220 to facilitate advancement and/or retraction of distal end region 210b into a blood vessel or other opening in tissue. As desired, a pigtail (not shown) may be provided on tip 220 to further aid atraumatic advancement of distal end region 210b.

Distal end region 210b of locator assembly 200 is selectably controllable between an unexpanded state, as shown in FIG. 8B, and an expanded state, as shown in FIG. 8C. As shown in FIG. 8B, when an expansion end 230 is in an unexpanded state, substantially flexible members 232 are substantially axially aligned with locator assembly 200. Alternatively, when expansion end 230 is in an expanded state, substantially flexible members 232 are flexed outward.

In some embodiments, material capable of being viewed using an imaging device may be incorporated into at least a portion of the locator assembly 200. For example, at least a portion of the tubular body 210 may include radiopaque material as a component of a coating over and/or a mixture with the material of the tubular body 210. Portions of other components of the locator assembly 200 may include material capable of being viewed using an imaging device as a component of a coating over and/or a mixture with their respective materials. In another example, at least a portion of the tip 220 of the locator assembly 200 and/or the substantially flexible members 232 of the expansion end 230 may include radiopaque material as a component of a coating over and/or a mixture with their respective materials.

Returning to FIG. 6B, a control member 250, such as a rod, wire, or other elongate member, may be moveably disposed within a lumen (not shown) formed by tubular body 210 and extending substantially between the proximal end region 210a (shown in FIG. 6A) and distal end region 210b (shown in FIG. 6A). Control member 250 may have proximal end region 250a coupled with a control block 260, and a distal end region (not shown) of control member 250 coupled with distal end region 210b of locator assembly 200, expansion end 230, and/or the movable end regions of substantially flexible members 232 (shown in FIGS. 8B-8C). Control block 260 may be formed of a metal or rigid plastic in a tubular shape, and may be adapted to be retained in control block cavity 265 formed on the internal surface of housing bottom half 380d, to thereby maintain control block 260 in a substantially fixed position relative to the housing 380 (as shown in FIG. 7). By moving tubular body 210 axially relative to control member 250, the distal end region 210b, expansion end 230, and/or the substantially flexible members 232 (FIG. 8B), are selectively transitioned between the unexpanded and expanded states.

With reference to FIG. 8A, a tubular body block 270 having proximal groove 271 may be formed on proximal end 210a (shown in FIG. 6A) of tubular body 210. Tubular body block 270 may be formed of metal, rigid plastic, or other substantially rigid material and may be formed integrally with or attached securely to tubular body 210. Proximal groove 271 and the proximal end of tubular body block 270 may have a shape adapted to cooperate with a pair of tabs 279a, 279b formed on a locator assembly block 280, whereby tubular body block 270 may be maintained in a fixed axial relationship with the locator assembly block 280. In this way, tubular body block 270 and tubular body 210 (FIG. 6B) may advance distally by distal advancement of locator assembly block 280.

A locator assembly spring 290 may be located coaxially with and may substantially surround a portion of tubular body block 270. Locator assembly spring 290 may be located between and in contact with the distal side of two of tabs 279a, 279b formed on locator assembly block 280 and the proximal side of locator assembly spring stop 381 formed on the inner surface of housing bottom half 380d. The locator assembly spring 290 so located may provide a force biasing to locator assembly block 280 in the proximal direction relative to housing 380.

Locator assembly block 280 may be formed of metal, plastic, or other rigid material. A function of locator assembly block 280 may be to allow a user to apply a force causing distal movement of tubular body 210 (FIG. 6A-6B) relative to control member 250 causing locator assembly 200 (FIG. 7) to transition from the unexpanded state to the expanded state. Slot 281 may be formed in the proximal end of locator assembly block 280. Slot 281 may have a size sufficient to accommodate control block 260 and control block cavity 265, and to allow locator assembly block 280 to travel axially relative to housing 380. As shown in FIGS. 6A-6B, the distal end of locator assembly block 280 may include a pair of distally extending legs 282a-b, with each of legs 282a-b having a ramp 283a-b on its inward facing surface. Finally, the locator assembly block 280 may have a pair of distally extending release tabs 284*a-b*, each of release tabs 284*a-b* having a detent 285*a-b*.

As shown in FIGS. 7-8A, locator assembly block 280 may be slidably received and retained within grooves formed in the proximal end of housing 380, with the proximal end of locator assembly block 280 extending from the proximal end of housing 380. Control block 260 and control block cavity 265 may be located in slot 281 formed in the proximal end of locator assembly block 280.

To release locator assembly 200, and enable it to slidably move within the grooves formed in the proximal end of the housing 380 and allow locator assembly 200 to transition from its expanded state to its unexpanded state, the apparatus 100 can include a locator release system 490 (FIG. 6A). Turning to FIG. 6A, locator release system 490 of the apparatus 100 may include locator release rod 491 having release tab spacer block 492 formed on its proximal end. Locator release rod 491 and release tab spacer block 492 may be received and retained in a groove formed on the interior surface of housing bottom half 380*d*. Release tab spacer block 492 may be integrally formed with or attached to the proximal end of locator release rod 491 and may be formed of metal, plastic, or other rigid material. Release tab spacer block 492 may have a shape and size adapted to fit between release tabs 284*a-b* formed on locator assembly block 280, thereby biasing release tabs 284*a-b* outward and causing outward facing detents 285*a-b* to engage retaining grooves 286*a-b* (FIG. 6B) formed on the interior of housing 380. As long as detents 285*a-b* are thus engaged with retaining grooves 286*a-b* in housing 380, locator assembly block 280 is held in an axial position against the spring force imparted in the proximal direction by locator assembly spring 290.

With continued reference to FIG. 6A, the distal end of locator release rod 491 may have an engagement member 493 that has an inward bend on the distal end of locator release rod 491. As described more fully below, engagement member 493 on locator release rod 491 may be positioned within the apparatus 100 such that when closure element 500 is delivered, engagement member 493 is engaged and caused to move axially in the distal direction, thereby disengaging release tab spacer block 492 from locator assembly block 280 and causing locator assembly 200 simultaneously to transition from an expanded state to an unexpanded state.

Returning to FIG. 6A, the carrier assembly 120 may be coupled with, and slidable relative to, locator assembly 200. Carrier assembly 120 may be configured to receive and retain closure element 500, which may be disposed substantially within carrier assembly 120. Carrier assembly 120 may be further configured to position closure element 500 substantially adjacent to an opening to be closed, and to deploy closure element 500. Upon being deployed, closure element 500 can maintain a reduced cross-section but may also temporarily and substantially uniformly expand beyond the natural cross-section of closure element 500. In either case, closure element 500, when deployed, can engage an amount of the blood vessel wall and/or tissue adjacent to the opening. Thereafter, closure element 500 may be configured to return to the natural cross-section, optionally substantially uniformly, such that the blood vessel wall and/or tissue are drawn substantially closed and/or sealed.

As shown in FIG. 6A, carrier assembly 120 may include a tube set 305 of at least one tubular member. For instance, the illustrated tube set can include carrier member 310, pusher member 320, cover member 330, and support member 340, also shown in FIG. 13. Carrier member 310, pusher member 320, cover member 330, and support member 340 may be provided as a plurality of nested, telescoping members with a common longitudinal axis. Carrier member 310 may be configured to receive and support an implantable device, i.e. closure element 500. In the present embodiment, proper positioning of the closure element 500 may include being disposed on the carrier member 310. Furthermore, proper positioning may include being disposed at a particular location along the carrier member 310. While being disposed on carrier member 310, closure element 500 may be deformed from the natural, planar configuration to form a substantially tubular closure element 500", as shown in FIGS. 19A-19G, and as described herein.

In some embodiments, material capable of being viewed by an imaging device may be incorporated into at least a portion of the carrier assembly 120. For example, at least a portion of the tube set 305 may include material capable of being viewed by an imaging device as a component of a coating over and/or a mixture with the material of the tube set 305. In this example, at least a portion of the carrier member 310, pusher member 320, cover member 330, and/or support member 340 may include radiopaque material as a component of a coating over and/or a mixture with their respective materials.

Returning to FIG. 6A, carrier member 310 may include a proximal end region (not shown) and distal end region (not shown). Carrier member 310 may also define lumen 314, which may extend substantially between the proximal end region and the distal end region of the carrier member 310 and configured to slidably receive at least a portion of tubular body 210 of locator assembly 200 and/or support member 340. Although the exterior cross-section of the carrier member 310 may be substantially uniform, the distal end region of carrier member 310 may have a cross-section that increases distally, as illustrated in FIG. 6A, for substantially uniformly expanding substantially tubular closure element 500 (FIG. 19G) beyond natural cross-section 530 (FIG. 19A) of closure element 500" when substantially tubular closure element 500" is deployed. Alternatively, distal end region of carrier member 310 may be formed with a uniform cross-section to deploy closure element 500 without cross-sectional expansion.

Pusher member 320 may have proximal end region (not shown) and distal end region (not shown). Pusher member 320 may be coupled with, and slidable relative to, carrier member 310. Pusher member 320 may include a predetermined length and a predetermined cross-section, both of which can be of any suitable dimension and can be configured to slidably receive carrier member 310 such that distal end region of pusher member 320 may be offset proximally from distal end region of carrier member 310. As desired, the predetermined length of pusher member 320 may be substantially equal to a predetermined length of carrier member 310. A predetermined length of pusher member 320 may be less than a predetermined length of carrier member 310 such that carrier member 310 and pusher member 320 may at least partially define a space distal to the distal end region of pusher member 320 and along the periphery of carrier member 310.

Pusher member 320 may be substantially tubular and can define a lumen 324 that may extend substantially between proximal end region of pusher member 320 and distal end region of pusher member 320 and configured to slidably receive at least a portion of the carrier member 310. The cross-section of pusher member 320 may be substantially uniform and distal end region of pusher member 320 can include one or more longitudinal extensions 325, which may extend distally from pusher member 320 and along the periphery of carrier member 310. Longitudinal extensions 325 may be biased such that longitudinal extensions 325 extend generally in parallel with the common longitudinal axis of carrier assembly 120. Longitudinal extensions 325 may be sufficiently flexible to expand radially, and yet sufficiently rigid to inhibit buckling as distal end region of pusher member 320 is directed distally along carrier member 310 and engages the distally-increasing cross-section of distal end region of carrier member 310 to deploy closure element 500. In the present embodiment, at least a portion of the longitudinal extensions 325 of the pusher member 320 may include material capable of being viewed by an imaging device as a component of a coating over and/or a mixture with the material of the longitudinal extensions 325.

Cover member 330 may be configured to retain closure element 500, in its generally tubular configuration, substantially within the carrier assembly 120 prior to deployment. Being coupled with, and slidable relative to, pusher member 320, cover member 330 has proximal end region (not shown) and distal end region (not shown), a predetermined length and a predetermined cross-section, both of which can be of any suitable dimension. Cover member 330 may be formed as a substantially rigid, semi-rigid, or flexible tubular member with an inner periphery and an outer periphery, and may define a lumen 334. Lumen 334 may extends substantially between proximal and distal end regions of cover member 330 and may be configured to slidably receive at least a portion of pusher member 320. When cover member 330 is properly positioned within carrier assembly 120, as schematically illustrated in FIG. 20A, distal end region may be configured to extend over a space, thereby defining annular cavity 370 for receiving and retaining substantially tubular closure element 500''. Proper positioning of the substantially tubular closure element 500'' may include positioning the substantially tubular closure element 500'' within the annular cavity 370 prior to deployment.

Figure 13:
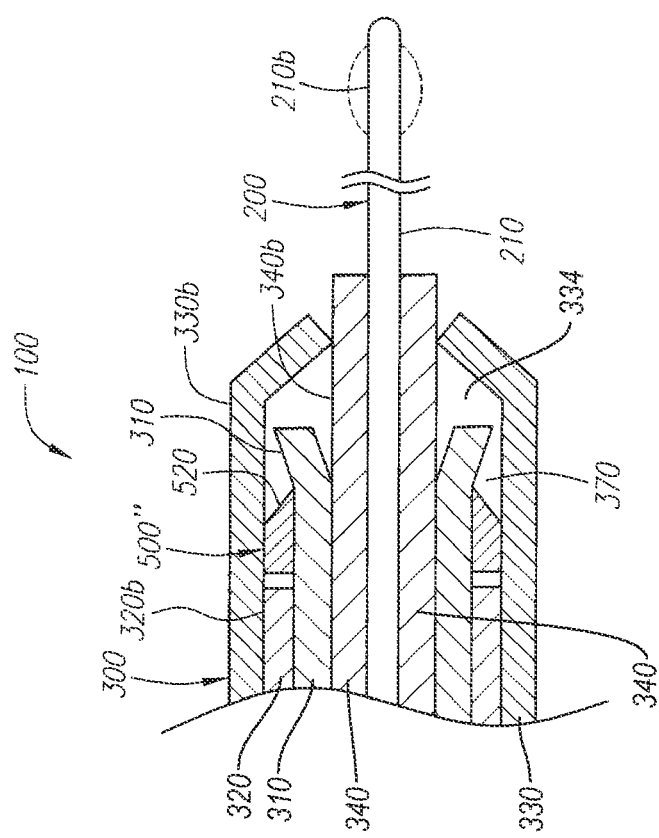
FIG. 13 illustrates a cross-sectional schematic view of the distal end of the apparatus shown in FIG. 9 as assembled for deployment.

The cross-section of cover member 330 may be substantially uniform, and distal end region of cover member 330 may include one or more longitudinal extensions 335, which extend distally from cover member 330 and along an outer periphery of pusher member 320, as shown in FIG. 13. Although longitudinal extensions 335 can extend generally in parallel with the longitudinal axis of the tube set 305, longitudinal extensions 335 may be biased such that the plurality of longitudinal extensions 335 extend substantially radially inward. Thereby, longitudinal extensions 335 may at least partially close lumen 334 substantially adjacent to distal end region of cover member 330. In the present embodiment, at least a portion of the longitudinal extensions 335 of the cover member 330 may include material capable of being viewed by an imaging device as a component of a coating over and/or a mixture with the material of the longitudinal extensions 335.

With reference to FIGS. 6B and 20A, to permit closure element 500 to be deployed from annular cavity 370, longitudinal extensions 335 may be sufficiently flexible to expand radially to permit distal end region of carrier member 310 to move distally past cover member 330 to open annular cavity 370 such that distal end region of cover member 330 no longer extends over the space 360.

When carrier assembly 120 is assembled as a plurality of nested, telescoping members, as shown in FIGS. 7 and 13, carrier member 310 is at least partially disposed within, and slidable relative to, a lumen of pusher member 320, and support member 340 is slidably relative to pusher member 310. Pusher member 320, in turn, is at least partially disposed within, and slidable relative to, lumen 334 of cover member 330. To couple carrier assembly 120 with locator assembly 200, tubular body 210 of locator assembly 200 may be at least partially disposed within, and slidable relative to, lumen 314. The longitudinal axis of locator assembly 200 may be substantially in axial alignment with the common longitudinal axis of carrier member 310, pusher member 320, and cover member 330.

The apparatus 100 may also include support member 340 as shown in FIG. 6A. Support member 340 may be configured to slidably receive tubular body 210 of locator assembly 200 and provide radial support for distal end region 210b of tubular body 210 when locator assembly 200 is coupled with the carrier assembly 120. Carrier assembly 120 can advantageously include support member 340, for example, if tubular body 210 is not sufficiently rigid or under other circumstances in which support for tubular body 210 might be desirable. It also will be appreciated that support member 340 may also be configured to inhibit longitudinal extensions 335, which extend from distal end region of cover member 330, from expanding prematurely when closure element 500 is deployed. If longitudinal extensions 335 were to expand prematurely, they may become hung up on an introducer sheath or other delivery member (if an introducer sheath or delivery member is used), the tissue, or the wall of the blood vessel. This may interfere with the proper advancement or other movement of cover member 330 and carrier assembly 120.

Support member 340 may be formed as a substantially rigid, semi-rigid, or flexible tubular member, and may include proximal end region 340a and distal end region 340b. Having an outer periphery, support member 340 may define lumen 344, extending substantially between proximal end region 340a and distal end region 340b and configured to slidably receive and support at least a portion of tubular body 210 of locator assembly 200. Support member 340, in turn, can be at least partially slidably disposed within lumen 314 of carrier member 310 such that tubular body 210 of locator assembly 200 is coupled with, and slidable relative to, carrier member 310 in the manner described in more detail above.

Support member 340 may have a predetermined length and a predetermined cross-section, both of which can be of any suitable dimension, and may have a substantially uniform cross-section. Although shown and described as being substantially separate for purposes of illustration, it will be appreciated that carrier member 310, pusher member 320, cover member 330, and/or support member 340 may be provided, in whole or in part, as one or more integrated assemblies.

With reference to FIG. 13, support member 340 may also include a distal end that is blunt, rounded and/or includes a radius or curved portion that may prevent and/or eliminate damage to tubular body 200 as tubular body is moved with respect to support member 340. In some cases during deployment, as discussed in more detail below, tubular body 200 may be inserted into a lumen of an introducer at such an angle as to require tubular body 200 to flex with respect to tube set 305 as much as between about 0 degrees and 90 degrees, preferably between about 10 degrees and 90 degrees and more preferably between 30 degrees and 60 degrees, for example when used in conjunction with a femoral artery. The above-described distal end of the distal end region 340b prevents and/or eliminates damage to tubular body 200 that may result from a sharp edge pressed along tubular body 200 during advancement of tube set 305, and more particularly, support member 340 and the distal end of the distal end region 340b.

Illustratively, the radii of the distal end of the support member 340 can have various sizes and configurations. In one configuration, the distal end radii can be about 0.002 inches.

In still another configuration, the distal end radii can be about 0.004 inches. In still another configuration, the distal end radii can be about 0.002 inches or greater. Increasing the radii of the distal end of support member 340 to about 0.004 inches, for instance, can decrease the amount of force required to overcome a bend in locator assembly 200 over those devices having a distal end radii of about 0.002 inches. This is because the larger radius on the distal end of the support member 340 may decrease the chance of the support member cutting into the tubular body 210 of the locator assembly 200.

In addition to the above, with the distal end having a radii greater than 0.002 inches, such as but not limited to 0.004 inches, there is a decrease in the possibility that the support member 340 may cut or otherwise damage the locator assembly 200 during positioning of the distal end of the apparatus 100 and subsequent deployment of the closure element 500. Further, a radii greater than 0.002 inches, such as but not limited to 0.004 inches, may not increase the forces used to split an introducer sheath and may not elongate the introducer sheath during positioning and deploying of the closure element 500.

With reference to FIGS. 6A and 6B, carrier assembly 120 may also include a portion of housing 380. For instance, the carrier assembly 120 can optionally include the top half 380c of housing 380, illustrated in FIG. 6A, and the bottom half 380d is shown in FIG. 6B. It will be understood, however, that housing 380 may be separate from the carrier assembly 120, while retaining and/or receiving all or a portion of the carrier assembly 120.

Housing 380 may be formed as an elongate member with a longitudinal axis, a periphery and may include proximal end region 380a and distal end region 380b. Thereby, when apparatus 100 is assembled, tubular body 210 of locator assembly 200 may be at least partially disposed within, and slidable relative to, tube set 305 such that distal end region 210b of tubular body 210 extends beyond distal end regions of the tube set 305. Tubular body 210, carrier member 310, pusher member 320, cover member 330, and, if provided, support member 340 may be at least partially disposed within, and slidable relative to, housing 380. Proximal end region 210a of tubular body 210 and proximal end regions of tube set 305 can be at least partially disposed within, and slidable relative to, housing 380. The distal end regions of the tubular body 210 and the tube set 305 may extend from distal end region 380b of housing 380 such that the common longitudinal axis (not shown) of tube set 305 may be substantially axially aligned with the longitudinal axis (not shown) of housing 380. When configured to slidably retain respective proximal end regions of the tubular body 210 and the tube set 305, housing 380 supports tube set 305 and can have one or more handles 391, 392 to facilitate use of apparatus 100. Handles 391, 392 may extend, optionally substantially radially, from the outer periphery of housing 380 and can be provided as illustrated or in any other manner.

To facilitate deployment of the closure element 500, the apparatus 100 can include a triggering system 400, shown in FIG. 7, which cooperates with a portion the locator assembly 200. For instance, a portion of locator assembly 200 and a portion of triggering system 400 may cooperate and be accessible externally to housing 380, as shown in FIGS. 6A and 6B. As shown in FIGS. 6A, 6B, and 9-12, triggering system 400 of apparatus 100 may be disposed substantially within housing 380. Triggering system 400 may be configured to control the relative axial movement and/or positioning of distal end regions of the tube set 305 and/or locator assembly distal end region 210b. Axial motion of one or more of carrier member 310, pusher member 320, cover member 330, and support member 340 and/or tubular body 210 may be attained, for example, by applying an axial force to triggering extension 405.

Triggering system 400 may include a set of block members including carrier block 410, pusher block 420, cover block 430, and support block 440, each of which may be formed integrally with or securely attached to its respective member of carrier assembly 120. The block members may be adapted to selectably couple and decouple carrier member 310, pusher member 320, cover member 330, and support member 340 relative to one another in order to provide axial movement of those components in a predetermined manner intended to deliver closure element 500 in the manner described herein. For example, when carrier assembly 120 reaches a first predetermined distal position, support member 340 may be decoupled from carrier member 310, pusher member 320, and cover member 330, and may be thereafter substantially inhibited from further axial movement. Thereby, carrier member 310, pusher member 320, and cover member 330 may be directed distally as support member 340 remains substantially stationary. Subsequently, carrier member 310 and cover member 330 can be decoupled from pusher member 320 and thereby inhibited from further axial movement. Pusher member 320 may be directed distally as support member 340, carrier member 310, and cover member 330 remain substantially stationary, as described more fully herein. These interactions may be monitored during deployment by the imaging device.

Carrier block 410 may be disposed on proximal end region of carrier member 310 and may include trigger extension 405, which extends through a slot in housing 380 to the exterior of housing 380, accessible by a user. This carrier block 410, as shown in FIG. 8A, may include a pair of grooves 413a-b, which may be formed on a peripheral surface of carrier block 410. These grooves 413a-b may be adapted to receive and retain a pair of tabs 445a-b formed on a pair of legs 444a-b extending distally from support block 440, thereby selectably coupling support block 440 to carrier block 410. Carrier block 410, as illustrated in FIG. 6A, may also include a pair of distal tabs 416a-b extending from the distal end of carrier block 410, and adapted to engage a pair of slots 423a-b formed on the proximal end of pusher block 420.

As shown in FIGS. 6A and 8A, carrier block 410 may also include a pair of arms 414a-b extending in the proximal direction from the proximal end of carrier block 410, each of arm 414a-b having an outward directed tab 415a-b at its proximal end. The tabs 415a-b may be adapted to selectably engage a pair of slots 387a-b (FIG. 6B) formed on the interior surface of housing 380 near its proximal end 380a and, when so engaged, to fix the axial position of carrier block 410 and, with it, carrier assembly 120 relative to housing 380. The tabs 415a-b may be disengaged from slots 387a-b FIG. 6B) in housing 380 when locator assembly block 280 is moved axially in the distal direction in the following manner. As locator assembly block 280 is advanced distally, the interior surfaces of the ramps 283a-b on locator assembly block legs 282a-b engage the exterior surfaces of tabs 415a-b and cause carrier block arms 414a-b to flex inward, releasing tabs 415a-b from the slots 387a-b in the housing, thereby freeing carrier block at 410 and carrier assembly 120 to move axially. Thus, axial movement of carrier block 410 within apparatus 100 may be inhibited until locator assembly block 280 is advanced to transition locator assembly 200 to the expanded condition, simultaneously releasing tabs 415a-b on carrier block 410.

Pusher block 420 may be disposed on proximal end region of pusher member 320. As described above, pusher block 420 may include a pair of slots 423a-b formed on its proximal end, and adapted to selectably engage distal tabs 416a-b extending from the distal end of carrier block 410. Pusher block 420 may also include a pair of grooves 424a-b formed on its peripheral surface, the grooves 424a-b being adapted to engage a pair of tabs 435a-b formed on a pair of forks 434a-b extending from the proximal side of cover block 430 to selectably couple cover block 430 to pusher block 420.

Cover block 430 may be disposed on proximal end region of cover member 330. As described above, cover block 430 may include a pair of forks 434a-b extending from the proximal end of the cover block 430, each of forks 434a-b having an inward directed tab 435a-b adapted to engage grooves 424a-b on the peripheral surface of pusher block 420 to selectably couple cover block 430 to pusher block 420.

Support block 440 may be disposed on proximal end region 340a of support member 340. As described above, support block 440 may include a pair of legs 444a-b extending from the distal end of the support block 440, each of legs 444a-b having an inward directed tab 445a-b adapted to engage grooves 413a-b formed on the surface of carrier block 410 to selectably couple support block 440 to carrier block 410.

Carrier block 410, pusher block 420, cover block 430, and support block 440 are shown in FIGS. 7, 8A, 9-10 in their fully coupled state, with support block 440 coupled to carrier block 410, pusher block 420 coupled to carrier block 410, and cover block 430 coupled to pusher block 420. In this arrangement, carrier assembly 120 may include a coaxial set of tubes as shown in FIG. 13, with support member 340 slidably retained substantially within carrier member 310, which is in turn slidably retained substantially within pusher member 320, which is in turn slidably retained substantially within cover member 330.

Triggering system 400 of apparatus 100 may include an energy storing element that is used in the final stage of closure element 500 delivery processes. The energy storing element, such as, but not limited to, a spring, such as pusher spring 425 shown in FIGS. 6A, 6B, 11 and 12, may be substantially retained in a spring cavity 417 formed in carrier block 410 and coaxially surrounds a proximal end region of carrier member 310. Pusher spring 425 is capable of expanding and contracting, storing potential energy as it is contracted and releasing energy as it expands. In its fully expanded state, the pusher spring 425 has a length that is greater than the length of spring cavity 417. The cross-sectional dimension of pusher spring 425 may be such that it backs up against and contacts the proximal end of pusher block 420. Thus, when pusher spring 425 is in place between carrier block 410 and pusher block 420, pusher spring 425 is capable of imparting a force biasing carrier block 410 away from pusher block 420.

Prior to delivery of closure element 500, the distal end of carrier block 410 may be in physical contact with the proximal end of pusher block 420. In this pre-delivery condition, pusher spring 425 is in a contracted state and may be maintained within spring cavity 417. A catch member 418 serves the function of maintaining the at carrier block 410 and pusher block 420 in the pre-delivery condition against the spring force of pusher spring 425, the force of which would otherwise force apart carrier block 410 from pusher block 420. Catch member 418 may be a U-shaped piece of metal, plastic, or other rigid material that engages first groove 419a formed on the surface of carrier block 410 and second groove 419b formed on the surface of pusher block 420. With reference to FIGS. 6A and 6B, pusher block 420 includes hole 426 extending through a portion thereof, with one end of hole 426 opening into groove 419b. Hole 426 is adapted to receive trip pin 427. During the closure element deployment process, trip pin 427 is advanced through hole 426, where it encounters catch member 418 retained in the groove 419b. Further advancement of trip pin 427 causes catch member 418 to become disengaged from groove 419b, thereby releasing the force of pusher spring 425.

The operation of the triggering system 400 of the apparatus 100 is illustrated in FIGS. 7-13 with the closure element 500 disposed substantially within the apparatus 100. As shown in FIGS. 7-8B, apparatus 100 has an initial position in which locator assembly block 280 is extended proximally and triggering system 400 is in its most proximal position. Accordingly, the locator assembly 200 is in its unexpanded state, as shown in FIG. 8B. At a point in time that the distal end region 210b of the locator assembly 200 has been positioned as desired (for example, within the blood vessel), locator assembly block 280 may be depressed distally, as shown in FIG. 9, thereby transitioning locator assembly 200 to the expanded state, as shown in FIG. 8C, and, simultaneously, releasing triggering system 400 from the initial position (in the manner described above) such that triggering system 400 can be advanced distally within the housing 380.

Triggering system 400 can then be advanced distally within housing 380, thereby advancing tube set 305 into position adjacent the blood vessel. At a first predetermined position, shown in FIGS. 9 and 10, support block 440 may encounter a support stop (not shown) on the interior surface of housing bottom half 380d that inhibits support block 440 from advancing further distally. As a result, an application of additional distal force to triggering system 400 may cause support block 440 to decouple from carrier block 410. More specifically, the tabs 445a-b on the legs 444a-b of support block 440 may disengage from grooves 413a-b on carrier block 410. Thus, support block 440 may remain in the position shown in FIGS. 9 and 10, while carrier block 410 may advance further distally upon application of force to triggering system 400.

Turning to FIGS. 11-13, as triggering system 400 is advanced further distally, cover block 430 may engage a cover stop on the interior surface near the distal end region 380b of housing 380, thereby inhibiting additional distal advancement of cover block 430. In addition, trigger extension 405 may engage handle 391 of the apparatus 100, thereby inhibiting additional distal advancement of carrier block 410.

Closure element 500 next may be deployed by releasing pusher spring 425, which may cause pusher block 420 (and, thus, pusher member 320 (FIG. 6A)) to advance distally, deploying closure element 500 in the manner described above. As previously described, pusher spring 425 may be released by disengaging catch member 418 from groove 419b on pusher block 420, thereby releasing pusher spring 425 to force the pusher block 420 and, thus, pusher member 320 distally relative to the carrier block 410. This action may cause pusher member 320 to deploy closure element 500 from within tube set 305. The catch member 418 may be disengaged from groove 419b by applying a force to a trigger 401, which, in the deployment position, may be aligned with trip pin 427 retained in pusher block 420. A trigger spring 402 may bias trigger 401 outward relative to housing 380, with a portion of the trigger 401 extending through a hole 130 (FIG. 6B) in housing 380. A user may apply an inward directed force to trigger 401 to counteract the biasing force of trigger spring 402 and force trigger 401 against the trip pin 427.

With reference to FIGS. 6A and 11, in addition to deploying closure element 500, the distal advancement of pusher block 420 may also cause locator release system 490 to activate, thereby transitioning locator assembly 200 from the expanded state to the unexpanded state. As pusher block 420 advances distally to deploy closure element 500 in the manner described above, pusher block 420 may also engage engagement member 493 of locator release system 490 and may advance locator release rod 491 distally. This action may cause release tab spacer block 492 to disengage from release tabs 284*a-b* on locator assembly block 280 (see FIG. 6A-6B), thereby releasing locator assembly block 280, which may return to its proximal position, causing locator assembly 200 to return to the unexpanded state. An indicator window (not shown) may be formed in housing 380 to give a visual indication that tab spacer block 492 has disengaged and that locator assembly 200 has returned to the unexpanded state. In the present embodiment, the deployment of closure element 500 and locator release actions may occur nearly simultaneously. These positions and interactions of the closure element delivery apparatus may be viewed, monitored, and/or analyzed using an imaging device as described above. Furthermore, material capable of being viewed by an imaging device may be incorporated into at least a portion of the components of the closure element delivery apparatus.

The following embodiment of a delivery apparatus may likewise illustrate various positions and interactions relating to a stent delivery apparatus. Referring now to FIGS. 14-18, an alternative embodiment of the apparatus is shown in accordance with the present invention. The apparatus of the alternative embodiment may be functionally similar to that of the device previously described above and shown in FIGS. 6A-13 in most respects, wherein certain features will not be described in relation to the alternative embodiment wherein those components may function in the manner as described above and are hereby incorporated into the alternative embodiment described below.

Generally, the apparatus 1000 illustrated in FIGS. 14-18 can accommodate for variations in the size of the physicians hand and grip by selectively reducing the distance between the device's handle portion and a portion of the triggering system usable to deploy the closure element and/or move a carrier assembly. Advancement of a locator assembly for locating the blood vessel wall prior to deploying the closure element may at least partially advance a portion of the triggering system of the apparatus including a trigger extension graspable by a physician or clinician. This partial movement may reduce the gap or throw between the trigger extension and the handle portion. In this manner, a physician or clinician may not need to stretch uncomfortably to position a thumb or finger on the trigger extension, grasping the handle portion, and maintaining the device in the desired orientation relative to the tissue and/or the puncture site. Furthermore, reducing the gap or throw between the trigger extension and the handle portion may enable the physician or clinician to more effectively apply a deploying force.

Figure 14:
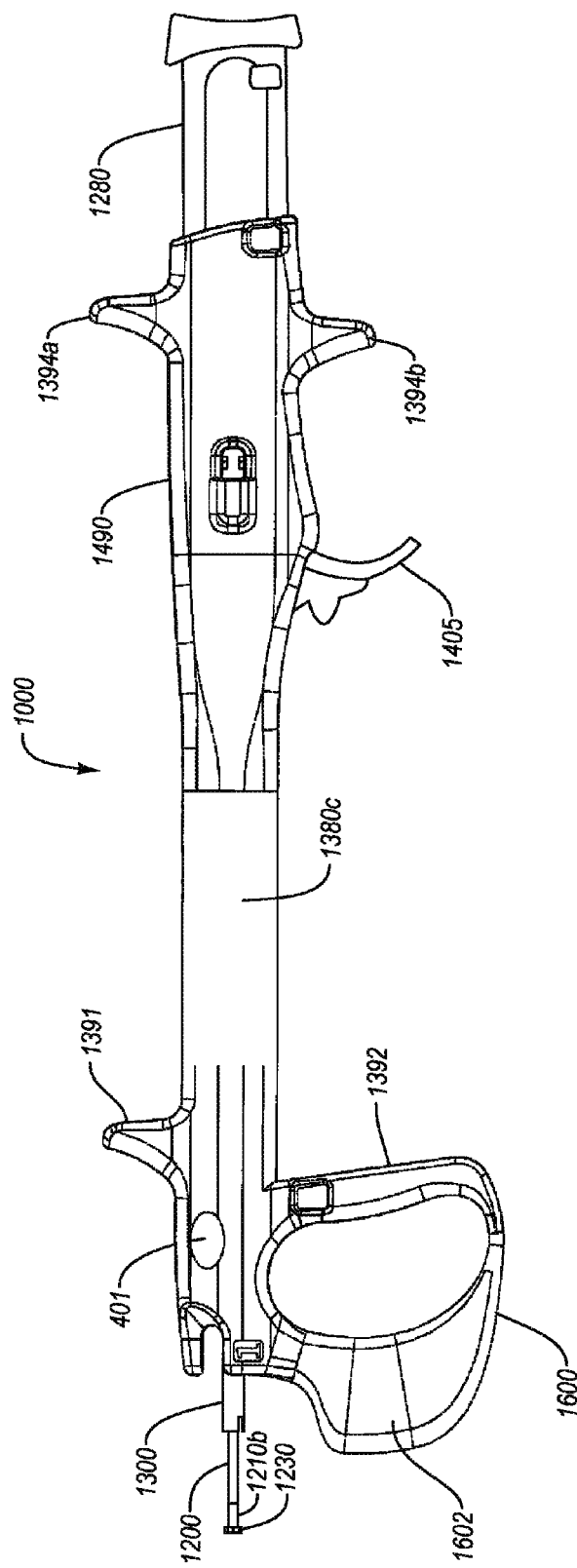
FIG. 14 illustrates a plan view of an alternative embodiment of an apparatus for closing openings in tissue in accordance with the present invention.
Figure 16A:
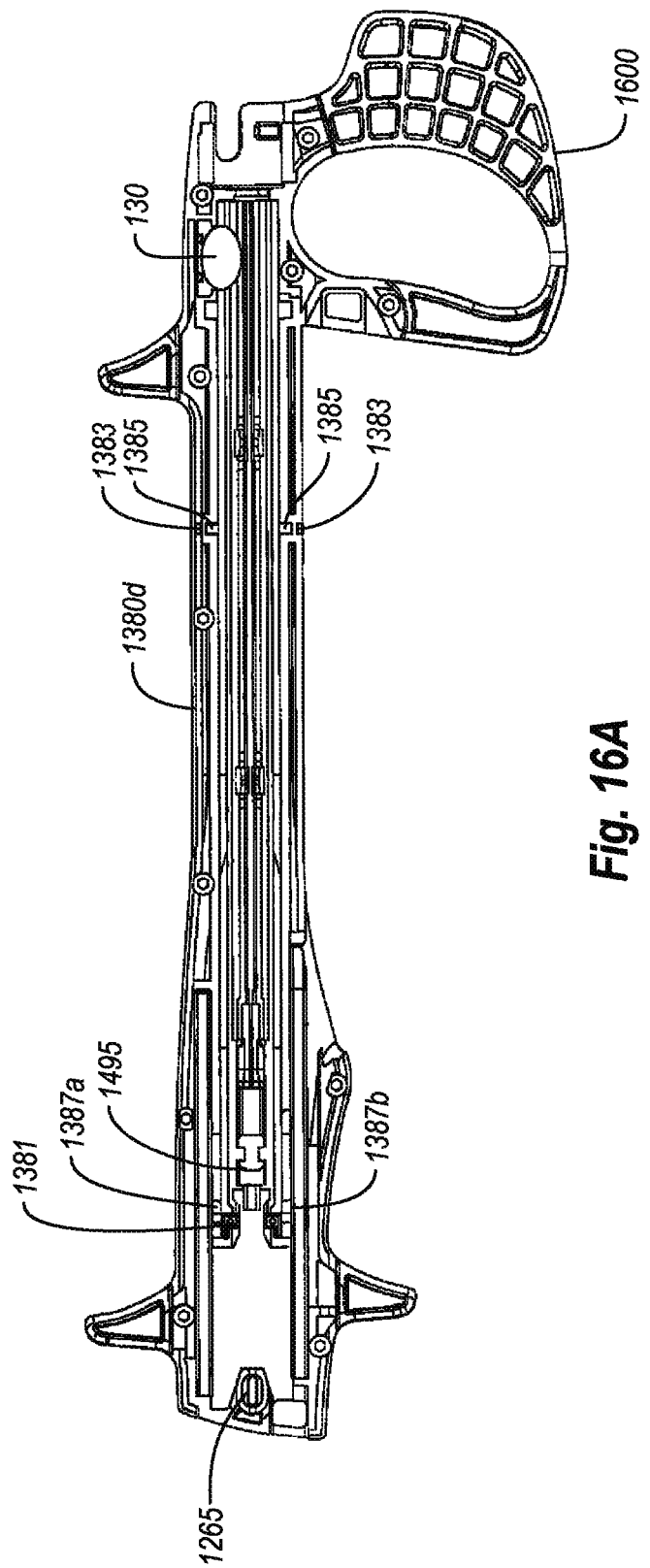
FIG. 16A illustrates a portion of a housing half of the alternative embodiment of FIG. 14, without certain functional components.

As shown in FIG. 14, the apparatus 1000 can include a housing 1380 that may include housing halves 1380*c* (shown in FIG. 14) and 1380*d* (shown in FIG. 16A). These housing halves 1380*c* and 1380*d*, either individually or collectively, can form one or more handles, hand grips, or finger portions which a physician or clinician can grip or hold to manipulate the apparatus 1000. As illustrated, the apparatus 1000 may include finger grip 1391 at a distal end and finger grips 1394*a* and/or 1394*b* on the proximal end of housing 1380 to facilitate use of locator assembly 1110, and specifically plunger 1280.

In addition, the apparatus 1000 may include handle, hand grip, and/or finger portion disposed on the distal end of housing 1380 configured to be engaged by a user when advancing housing 1380 to deploy closure element 500 (FIG. 6A). This handle, handle portion, and/or hand grip portion may include a shaped grasping portion 1600 and an elongate grasping portion 1392 spaced apart from the shaped grasping portion 1600. Each of the grasping portions 1392 and 1600 may be contoured to be received by a user's hand. For instance, the grasping portion 1600 may provide a stable base upon which the physician or clinician can move the device or apparatus as the closure element 500 is positioned and deployed. This grasping portion 1600 may have a shaped portion 1602 with a curved configuration that can receive at least a thumb or finger of the physician or clinician as the physician or clinician holds the apparatus 1000. The curved configuration or profile may allow the physician to grasp the handle or handle grip portion while resting their hand, wrist, or forearm upon a patient during the procedure, such as deployment of the closure element 500, thereby providing stability during use of the apparatus 1000.

It will be understood that although reference is made to one particular configuration of the handle, hand grip, and/or finger portions, various other handle portion configurations may perform the function of providing a stable base for manipulation of the apparatus 1000. For instance, and not by way of limitation, the handle portion may be planar rather than curved. Further, the handle portion may include one or more finger receiving holes. In addition, the handle portion may include a material to provide cushioning or comfort to the physician and/or clinician. For example, flexible, yielding, and/or elastic materials may be formed or applied to all or a portion of the handle portion.

Figure 15:
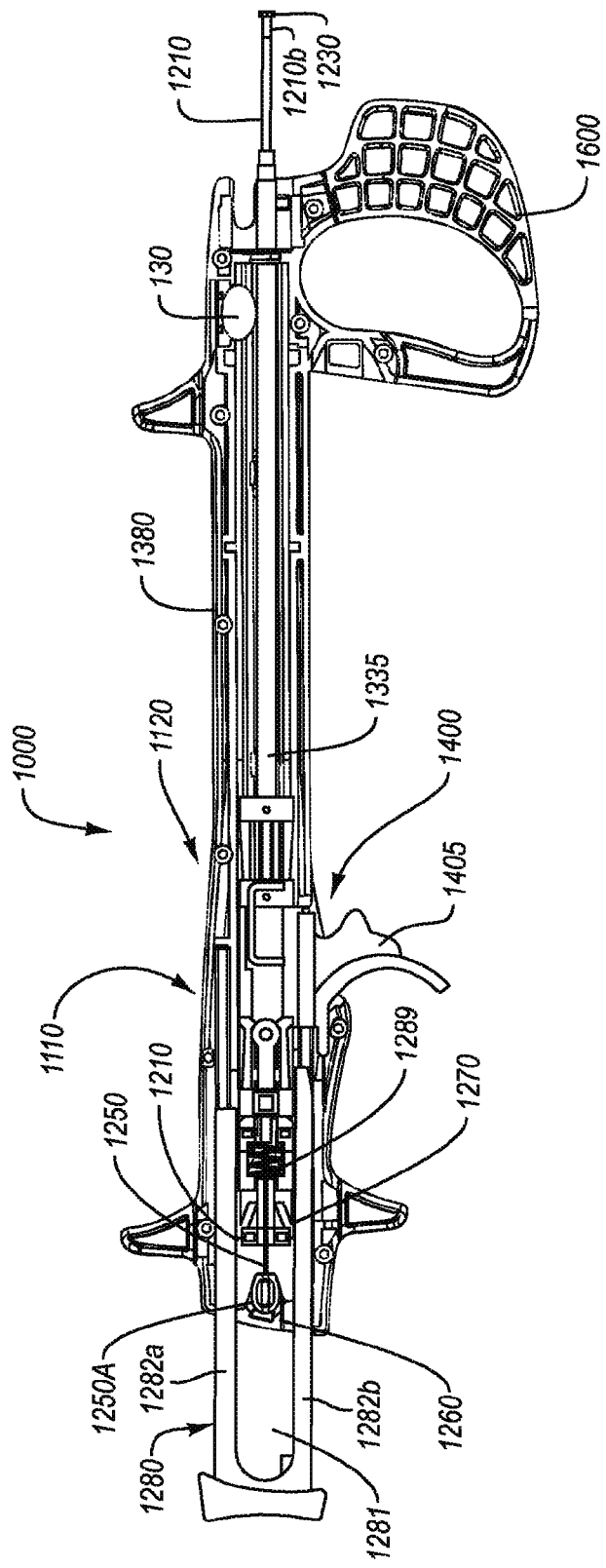
FIG. 15 illustrates a portion of a housing half of the alternative embodiment of FIG. 14, illustrating the functional components thereof.

Referring now to FIGS. 14 and 15, apparatus 1000 may be provided as one or more integrated components and/or discrete components. For instance, and not by way of limitation, apparatus 1000 may include locator assembly 1110 and/or carrier assembly 1120. For purposes of illustration, locator assembly 1110 and carrier assembly 1120 are shown in FIG. 15 as having substantially separate assemblies. As desired, however, locator assembly 1110 and carrier assembly 1120 may each be provided, in whole or in part, as one or more integrated assemblies. Portions of locator assembly 110 and/or carrier assembly 120 may also be used as part of apparatus 1000. Alternatively, modified versions of locator assembly 110 and/or carrier assembly 120 may be used.

Locator assembly 1110 may be constructed in the manner previously described above, including a flexible or semi-rigid tubular body (such as an elongate rail) with a longitudinal axis. The tubular body may have a proximal end region and a distal end region and/or may include a predetermined length and a predetermined outer cross-section, both of which may be of any suitable dimension. The distal end region of the locator assembly may include a substantially rounded, soft, and/or flexible distal end or tip to facilitate atraumatic advancement and/or retraction of the distal end region into a blood vessel or other opening in tissue. As desired, a pigtail (not shown) may be provided on the distal end to further aid atraumatic advancement of the distal end region. The distal end region of locator assembly 1110 may be selectably controllable between an unexpanded state and an expanded state.

As shown in FIG. 15, apparatus 1000 may include carrier assembly 1120 which may be functionally equivalent to carrier assembly 120 (FIG. 6A) described above and will not be described in detail with regard to the present embodiment. As with carrier assembly 120, carrier assembly 1120 may be coupled with and/or be slidable relative to locator assembly 1110. Carrier assembly 1120 may be configured to receive and retain the closure element 500 (shown in FIGS. 19A-19G), which may be disposed substantially within carrier assembly 1120. Carrier assembly 1120 may function to position closure element 500 substantially adjacent to an opening to be closed, and to deploy closure element 500.

Figure 16B:
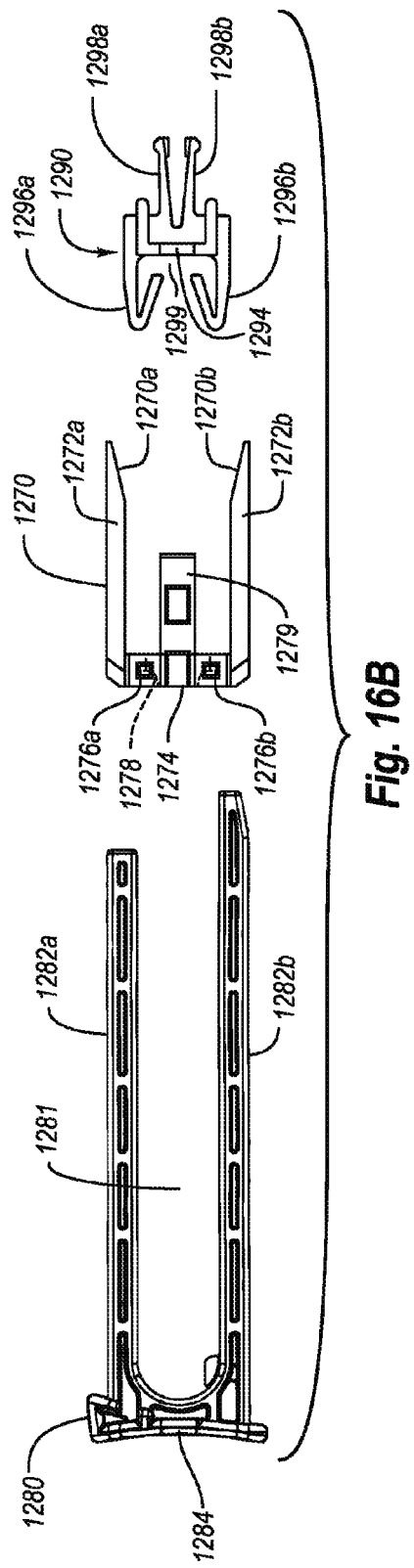
FIG. 16B illustrates a portion of a locator control system of the alternative embodiment of FIG. 14.
Figure 16C:
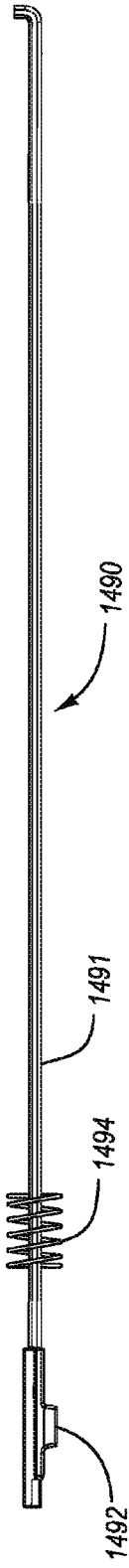
FIG. 16C illustrates a portion of a locator release system of the alternative embodiment of FIG. 14.

Referring now to FIGS. 15 and 16, locator assembly 1110 of the present embodiment will be described in greater detail. As with the previous locator assembly 110, a control member 1250, such as a rod, wire, or other elongate member, may be moveably disposed within a lumen (not shown) formed by tubular body 1210 and may extend substantially between the proximal end region and the distal end region of the lumen. Control member 1250 may have a proximal end region 1250*a* that may be coupled with a control block 1260, and a distal end region that may be coupled with the distal end region of locator assembly 1110, expansion members 1230, and/or movable end regions of substantially flexible members, such as flexible members 232 (FIG. 8B). Control block 1260 may be constructed in a tubular shape and formed of a metal or rigid plastic, and may be adapted to be retained in control block cavity 1265 (FIG. 16A) formed on the internal surface of the housing half 1380*d*, to thereby maintain control block 1260 in a substantially fixed position relative to housing half 1380*d* and so housing 1380. The locator assembly 1110 may selectively transition distal end region 1210*b*, expansion members 1230, and/or the substantially flexible members between the unexpanded and expanded states by moving tubular body 1210 axially relative to control member 1250. Additionally as shown in FIG. 16A, apertures 1383 may be placed adjacent to and/or in communication with detents 1385, wherein in use as described below, tabs 415*a* and 415*b* (FIG. 6A) may engage the detents 1385 during use. Apertures 1383 may be configured to receive the tip of a medical device, such as a tip of a dilator from a sheath assembly, wherein the tip of the dilator may be used to disengage the tabs 415*a* and 415*b* (FIG. 6A) from the detents 1385 thereby releasing the locked position of the device. This may enable a user to move the trigger assembly 1400 (FIG. 15) proximally (toward the user) after the clip has been deployed in the event that the device becomes stuck within the patient, thereby providing a safety release mechanism. It shall be appreciated that the apertures 1383 may be replaced by other features such as recessed buttons that become exposed with the engagement of the tabs with the detents and/or a specific tool may be provided with the device.

With reference to FIGS. 15 and 16B, to facilitate movement of carrier assembly 1120 to reduce the distance between a trigger extension 1405 and the distal end of housing 1380, the functionality of locator assembly block 280 (FIG. 6A) may be provided through the combination of a plunger 1280, a tubular body block 1270, and a spring retainer 1290. In addition to providing the functionality of locator assembly block 280, including controlling movement of expansion members 1230, plunger 1280, tubular body block 1270, and spring retainer 1290 and/or aiding with moving trigger extension 1405 toward the distal end of housing 1380.

With reference to FIG. 16B, plunger 1280 may include two spaced apart legs 1282*a-b*, which may be separated by a plunger member 1284 to form a slot 1281 therebetween. The legs 1282*a-b* may be spaced apart sufficiently to accommodate and/or receive a portion of tubular body block 1270 and/or spring retainer 1290 therebetween. Each of the legs 1282*a-b* may have a stepped configuration, such as the configuration shown in FIG. 16D. Plunger 1280 may be slidably received and/or retained within grooves formed in the proximal end of housing 1380, with the proximal end of plunger 1280 extending from the proximal end of housing 1380.

Plunger 1280 may be constructed of metal, plastic, and/or other rigid materials. The proximal end of plunger 1280 may have a slot 1281 formed therein. Slot 1281 may have a size sufficient to accommodate control block 1260 and control block cavity 1265 and to allow plunger 1280 to travel axially relative to housing 1380. As mentioned, the distal end of plunger 1280 may include a pair of distally extending legs 1282*a-b* with optional ramps 1283*b* on respective outward facing surfaces. In addition, a recess 1285 may be formed in each leg 1282*a-b* within which a protrusion 1286 may move. The protrusion 1286 may have a detent 1288 that can interlock with the tubular body block 1270 and/or spring retainer 1290 as plunger 1280 is moved distally.

Figure 17:
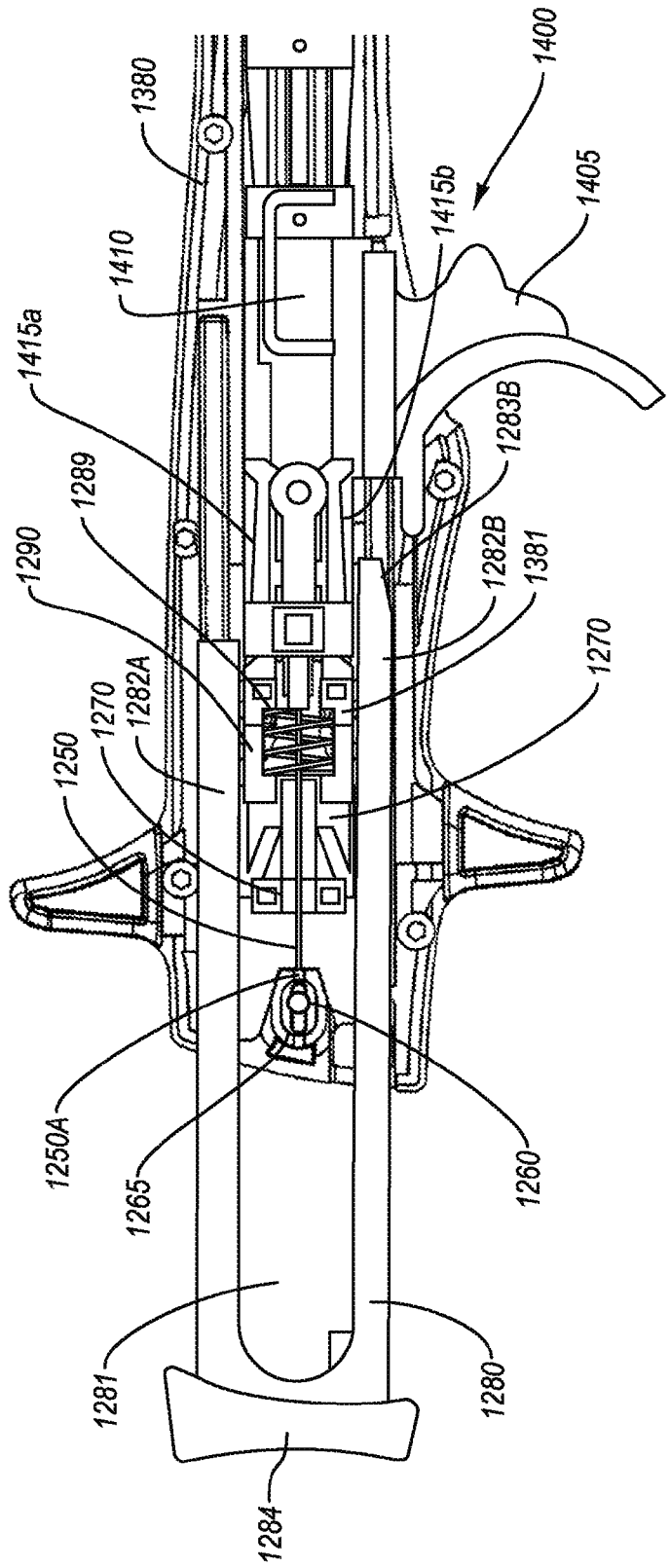
FIG. 17 illustrates a close-up cross-sectional view of the proximal end of the apparatus shown in FIG. 14, illustrating the initial position of the locator control system.

With reference to FIGS. 16B and 16E, tubular body block 1270 may be formed integrally with or attached securely to tubular body 1210. The tubular body block 1270 may include a pair of extending legs 1272*a-b*. Each of legs 1272*a-b* may have a ramp portion 1273*a-b* on its inward facing surface. Ramp portions 1273*a-b* may cooperatively engage tabs, not shown but similar to tabs 415*a-b* (FIG. 6A), of carrier block 1410 (FIG. 17). In an initial state, the tabs 415*a-b* (FIG. 6A) may be engaged in slots 1387*a*-1387*b* (FIG. 16A) formed in housing half 1380*d* to hold triggering system 1400 (FIG. 15) in a fixed axial relationship with housing 1380.

An intermediate member 1274 may extend between legs 1272*a-b*. The intermediate member 1274 may include a pair of upwardly extending extensions 1276*a-b* and/or a tab 1278, shown in dotted lines in FIG. 16B. Extensions 1276*a-b* may be received within the space between legs 1282*a-b* of plunger 1280. Stated another way, tubular body block 1270 may be held in a fixed axial relationship with respect to plunger 1280 through the engagement of legs 1282*a-b* and legs 1272*a-b*. The tab 1278 may be adapted to cooperate with spring retainer 1290 and/or lock with a portion of spring retainer 1290 as plunger 1280 moves distally, as will be described in more detail hereinafter.

A tubular portion 1279 may extend from intermediate member 1274 in the same direction as legs 1272*a-b*. The tubular portion 1279 may slidably cooperate with spring retainer 1290 and may receive tubular body 1210 within a lumen. Further, tubular portion 1279 may cooperate with a locator assembly spring 1289 (FIG. 15) which may bias tubular body block 1270 and/or spring retainer 1290 relative to housing 1380.

As shown in FIGS. 16B and 16F, spring retainer 1290 may include a wall portion 1291 with a recess 1292 that may receive tubular portion 1279 of tubular body block 1270. The wall portion 1291 may define a channel 1294 within which the locator assembly spring 1289 (FIG. 15) may be received. For instance, locator assembly spring 1289 (FIG. 15) may extend from wall portion 1291 to locator assembly spring stop 1381 (FIG. 16A) to bias movement of spring retainer 1290, tubular body block 1270, and/or locator assembly 1110.

Spring retainer 1290 may further include arms 1296*a-b*. Arms 1296*a-b* may include a movable portion 1297*a-b* that may flex or move to receive tab 1278 of tubular body block 1270. For instance, tab 1278 may include curved surfaces that may cooperate and/or receive a portion of movable portion 1297*a-b* as tubular body block 1270 moves relative to spring retainer 1290. Alternatively, tab 1278 may be positioned within a space 1299 between wall portion 1291 and movable portion 1297*a-b* before manipulation or operation of apparatus 1000. It will be understood that other portions of arms 1296*a-b* can flex or move, whether or not movable portions 1297*a-b* move.

In addition to arms 1296*a-b*, spring retainer 1290 may include release tabs 1298*a-b*. These release tabs 1298*a-b* may function in a similar manner to tabs 284*a-b* (FIG. 6A). For instance, tabs 1298*a-b* may cooperate with a locator release system 1490 in a manner substantially similar to the embodiments described above. For example, release tabs 1298*a-b* may engage release cavity 1495 on housing 1380, and may be held from releasing by release tab spacer block 1492.

Generally, plunger 1280, tubular body block 1270, and/or spring retainer 1290 may be formed of metal, plastic, and/or other material, whether rigid, substantially rigid, or flexible. As such, plunger 1280, tubular body block 1270, and/or spring retainer 1290 may be formed from medical grade synthetic materials and/or materials that can be sterilized or otherwise cleaned.

Figure 18:
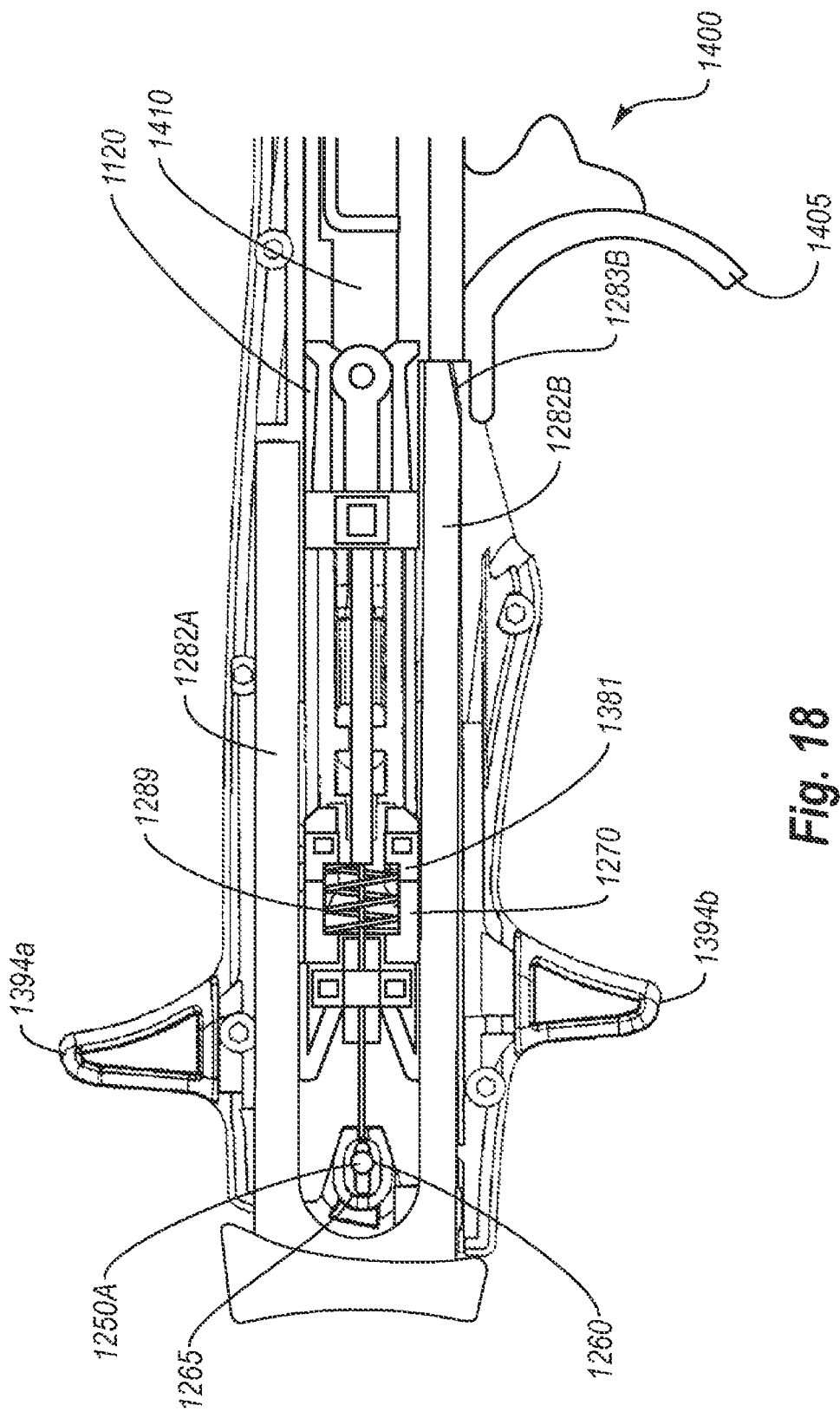
FIG. 18 illustrates a close-up cross-sectional view of the proximal end of the apparatus shown in FIG. 14, illustrating the final position before clip release of the locator control system.
Figure 19A:
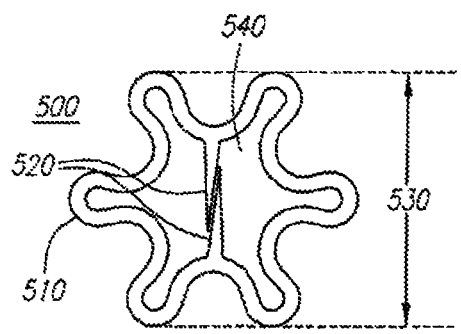
FIGS. 19A-19G illustrate various embodiments of closure elements that can be utilized with the apparatus of the present invention.
Figure 19B:
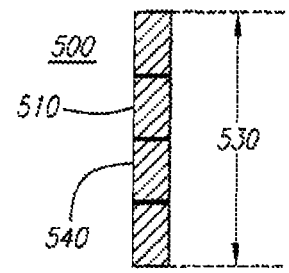
Figure 19C:
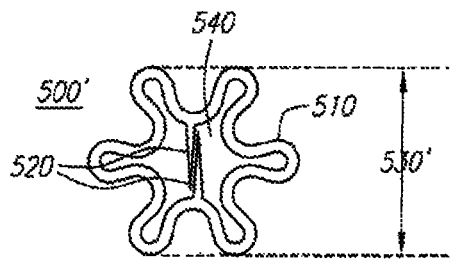
Figure 19D:
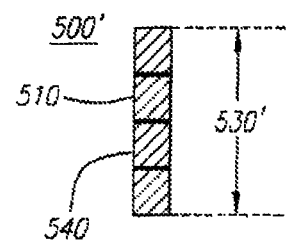
Figure 19E:
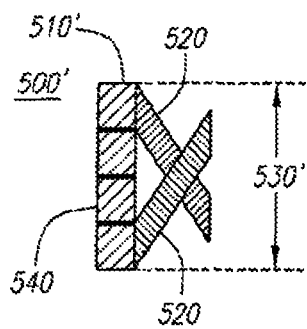
Figure 19F:
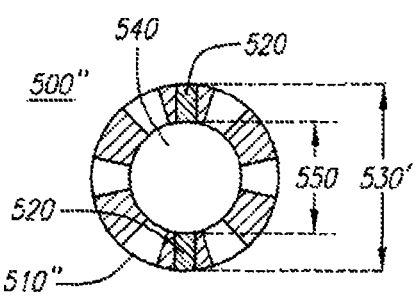
Figure 19G:
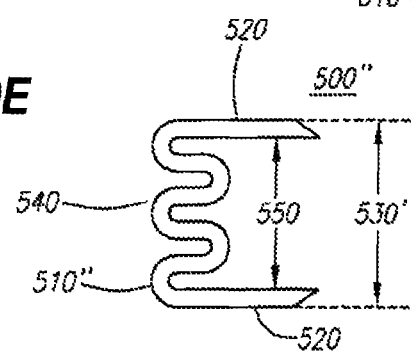

Turning now to FIGS. 17 and 18, illustrated are the operational positions of the apparatus 1000 in (i) an initial state with the expansion members 1230 (FIG. 14) in an unexpanded condition and (ii) a state with the expansion members 1230 (FIG. 14) in an expanded condition.

With reference to FIG. 17, in the initial state, plunger 1280 may extend from the distal end of housing 1380, expansion members 1230 (FIG. 15) may be in an unexpanded condition, and locator assembly spring 1289, which can be located coaxially with tubular body block 1270, may be located between spring retainer 1290 and the proximal side of locator assembly spring stop 1381 formed on the inner surface of housing bottom half 1380*d*. In this initial state, locator assembly spring 1289 may be held in a biased state. Optionally, a portion of carrier assembly 1120 (FIG. 15) may be associated with legs 1282*a-b* of plunger 1280 and contact carrier a portion of carrier assembly 1120 (FIG. 15).

Once a user presses on plunger 1280 to expand expansion members 1230, i.e. moving plunger 1280 toward expansion members 1230, tubular body block 1270 and/or tubular body 1210 may advance distally by distal advancement of plunger 1280. Upon advancement, and with reference to FIGS. 6A and 15-17, ramp members 1273*a-b* may press tabs 415*a-b*, which are hidden by plunger 1280 in FIG. 17, releasing carrier block 1410 to slide axially in housing 1380. Advancing ramp members 1273*a-b* may release tabs 1298*a-b* engaged in retaining grooves 1387*a-b* in cooperation with locator release system 1490. Locator release system 1490 may be functionally equivalent to locator release system 490 described above. Thus, advancing ramp members 1273*a-b* may thereby fix spring retainer 1290 and tubular body block 1270 axially with respect to housing 1380 and expansion members 1230 of locator assembly 1110 in an expanded state. Also during advancement, tab 1278 of tubular body block 1270 may advance between arms 1296*a-b* of spring retainer 1290. This advancement may extend the arms outwardly until tab 1278 advances past the ends of arms 1296*a-b*, which may cause arms 1296*a-b* to extend behind tab 1278, thereby coupling spring retainer 1290 and tubular body block 1270, and fixing tubular body block axially prior to activation of locator release system 1490. Once advanced, the plunger 1280, in the present embodiment, may be locked into a distal position by legs 1272*a* and 1272*b*.

Further axial movement of plunger 1280 may allow the engagement of distal end of leg 1282*b* and carrier block 1410, thereby moving carrier block 1410 distally along with carrier assembly 1120, as illustrated in FIG. 18. This additional movement of carrier assembly 1120 may also move trigger extension 1405, generally shortening the distance required to fully engage the carrier assembly 1120. Combining the deployment of locator assembly 1110 and the partial advancement of carrier assembly 1120 in a single step, may allow for a reduction in travel of the trigger block and trigger extension 1405. This reduction of travel may allow for a greater variation in user strength as well as the physical size of a users hand to fit better with device 1000 as illustrated.

Once locator assembly 1110 is deployed, carrier assembly 1120 may be advanced distally by exerting force on trigger extension 1405, and may be fixed in the distal position in the manner described above with reference to other embodiments above. After the locator has been deployed and the carrier assembly initially advanced, as shown in FIG. 18, device 1000 may function in the manner described above with regard to other embodiments of the present invention and thus will not be described in detail with regard to this embodiment.

In some embodiments, the tubular body block and the release block may be integrally formed. When the tubular body block and the release block are integrally formed, axial movement of the locator assembly block may force outward movement of tabs holding the tubular body block to the locator assembly block, which may allow the integrally formed tubular body block and release block to slide distally with respect to the locator assembly block and may cause the release tabs to load the locator release system to release as discussed above.

Referring now to FIGS. 19A-19G illustrating embodiments of a closure element that can be used as part of or with the apparatus 100. The closure element, generally identified with reference numeral 500, may have a generally annular-shaped body defining a channel and one or more barbs and/or tines for receiving and engaging the blood vessel or other body lumen wall and/or the tissue around the opening. Although the closure element has a natural shape and size, the closure element can be deformed into other shapes and sizes, as desired, and can be configured to return to the natural shape and size when released. For example, closure element 500 can have a natural, planar configuration with opposing tines and a natural cross-section. The closure element 500 can be formed from any suitable material, including any biodegradable material, any shape memory material, such as alloys of nickel-titanium, or any combination thereof. Additionally, it is contemplated that the closure element 500 may be coated with a beneficial agent or be constructed as a composite, wherein one component of the composite would be a beneficial agent. Exemplary embodiments of a closure element 500 are disclosed in U.S. Pat. Nos. 6,197,042, 6,623,510, 6,461,364, 6,391,048, 6,719,777, and 7,211,101 and U.S. Patent Publication No. 2004-153122. The disclosures of these references and any others cited therein are expressly incorporated herein by reference in their entireties.

In some embodiments, material that is capable of being viewed by an imaging device may be incorporated into at least a portion of the closure element 500. For example, radiopaque material and/or dense material may be included as a component of a mixture that may be incorporated into the material of the closure element. In embodiments where the closure element is formed from a sheet of material, the sheet of material may include material that is capable of being viewed by an imaging device as a component of the material. In embodiments where the closure element 500 is formed from a wire as described in U.S. Pat. No. 6,719,777, the wire may include material that is capable of being viewed by an imaging device as a component of the wire.

In other embodiments, at least a portion of the closure element 500 may include a coating that includes material that is capable of being viewed by an imaging device as a component of the coating. For example, a coating of radiopaque material and/or dense material may be applied to a portion of the surface of the closure element 500. Coatings may be applied using various coating methods. Coating methods may include physical vapor deposition, chemical vapor deposition, ion beam assisted deposition, electroplating and/or other coating methods. Physical vapor deposition may include sputter deposition and/or other physical vapor deposition methods.

FIGS. 20A-20K illustrate examples of proper positions and/or interactions relating to an implantable device, i.e. a closure element 500, and/or components of a delivery apparatus, i.e. a closure element delivery apparatus 100. Other positions and/or interactions may be used.

As described previously, and with reference to FIG. 20A, closure element 500 may be disposed within the carrier assembly and adjacent to the distal end of pusher tube 320. As shown in FIG. 20A, for example, the reduced closure element 500 may be slidably received over distally-increasing cross-section of distal end region of carrier member 310 and may be disposed about periphery 312 of carrier member 310 adjacent to an annular cavity 370. Since reduced cross-section 530 of reduced closure element 500 is less than cross-section of distally-increasing cross-section, reduced closure element 500 may be temporarily radially deformed to be received over distal end region of the carrier member 310. Also, as reduced closure element 500' (FIG. 19C) is received over distal end region of carrier member 310, opposing tines 520 of reduced closure element 500' (FIG. 19C) engage distal end region of carrier member 310. Reduced closure element 500' (FIG. 19C) may thereby form substantially tubular closure element 500", illustrated in FIG. 19G, with the ends of the barbs and/or tines extending towards the distal end of the apparatus 100.

The apparatuses of the present invention may be configured to be utilized with a sheath. The sheath may be inserted or otherwise positioned into an opening in a body having a lumen. The sheath may generally have a substantially flexible or semi-rigid tubular member having a proximal end region and a distal end region and may include a predetermined length and/or a predetermined cross-section, both of which can be of any suitable dimension. The sheath may form a lumen that may extend along a longitudinal axis of the sheath and/or substantially between the proximal and/or distal end regions. The lumen may have any suitable internal cross-section and may be suitable for receiving one or more devices (not shown), such as a catheter, a guide wire, and/or other device. The lumen may be configured to slidably receive the tubular body of the locator assembly and/or the tube set of the carrier assembly of the devices in accordance with the present invention.

Since the internal cross-section of the sheath may be less than or substantially equal to the predetermined cross-section of the cover member, the sheath may be configured to radially expand, such as by stretching, to receive the tube set. Alternatively, or in addition, the sheath may be advantageously configured to split as the tube set is received by and advances within the lumen of the sheath. This may permit the apparatuses to access the body lumen wall. To facilitate the splitting, the sheath may include one or more splits, such as longitudinal splits. Each split may be configured to split the sheath in accordance with a predetermined pattern, such as in a spiral pattern. It will be appreciated that when the internal cross-section of the sheath is greater than the predetermined cross-section of the cover member, it may not be necessary for the sheath to be configured to radially expand and/or split. In some embodiments, the apparatus may include a cutting means that initiates a tear line or split in the sheath when the sheath is engaged with the distal end of the apparatus.

The sheath may be advanced over a guide wire or other rail (not shown), which has been positioned through the opening and into the blood vessel using conventional procedures such as those described above. In some embodiments, the blood vessel may be a peripheral blood vessel, such as a femoral or carotid artery. In other embodiments, other body lumens may be accessed using the sheath. The opening, and consequently the sheath, may be oriented with respect to the blood vessel to facilitate the introduction of devices through the lumen of the sheath and into the blood vessel with minimal risk of damage to the blood vessel. One or more devices (not shown), such as a catheter, a guide wire, and/or other devices, may be inserted through the sheath and/or advanced to a preselected location within the patient's body. For example, the devices may be used to perform a therapeutic and/or diagnostic procedure, such as angioplasty, atherectomy, stent implantation, and/or other procedures, within the patent's vasculature.

FIGS. 20A-20K illustrate one exemplary manner to deploy closure element 500 by apparatuses according to the present invention. For purposes of continuity, reference numbers to the first discussed embodiment are used, but it will be evident that other embodiments may be used in a similar fashion.

A sheath 640 may be inserted or otherwise positioned through a patient's skin 650 and tissue 630 and within the blood vessel 600 or other body lumen via the opening 610. This may provide access to the blood vessel 600 through the blood vessel wall 620 for performance of a therapeutic and/or diagnostic procedure.

After the procedure is completed, the devices associated with the therapeutic and/or diagnostic procedure may be removed from sheath 640 and apparatus 100 may be prepared to be received by lumen 644 of the sheath. Being in the unexpanded state, the distal end region 210b of tubular body 210 of the locator assembly 200 may be slidably received by the lumen and atraumatically advanced distally into the blood vessel 600, as illustrated in FIG. 20B. Once the distal end region 210b extends into blood vessel 600, distal end region 210b may transition from the unexpanded state to the expanded state by activating the switching system of locator assembly 200, as illustrated in FIG. 20C. As discussed with reference to the embodiments described in reference to FIGS. 14-18, the carrier assembly may be partially advanced when the locator assembly 200 is transitioned from the unexpanded to the expanded state by pressing the locator assembly block distally with respect to the housing.

Turning to FIG. 20D, apparatus 100 and/or sheath 640 may be retracted proximally until distal end region 210b is substantially adjacent to an outer surface 620b of blood vessel wall 620. Distal end region 210b may thereby draw the blood vessel wall 620 taut and may maintain the proper position of apparatus 100 as blood vessel 600 pulsates. Since the expanded cross-section of distal end region 210b is greater than or substantially equal to the cross-section of opening 610 and/or the cross-section of lumen 644, distal end region 210b may remain in blood vessel 600 and may engage inner surface 620b of blood vessel wall 620. Distal end region 210b may frictionally engage inner surface 620b of blood vessel wall 620, thereby securing apparatus 100 to blood vessel 600. Sheath 640 can be retracted proximally such that distal end region 640b of sheath 640 is substantially withdrawn from blood vessel 600, permitting apparatus 100 to access blood vessel wall 620.

Once distal end region 210b of locator assembly 200 contacts inner surface 620b of blood vessel wall 620, tube set 305 may then be advanced distally and/or received within lumen 644 of sheath 640. In the manner described above, sheath 640 may radially expand and/or split in accordance with the pre-determined pattern as tube set 305 advances because the internal cross-section of sheath 640 is less than or substantially equal to pre-determined cross-section of cover member 330. Being coupled, carrier member 310, pusher member 320, cover member 330, and support member 340 may each advance distally and approach the first predetermined position, as illustrated in FIG. 20F. As discussed with reference to the embodiments described in reference to FIGS. 14-18, a stable base may be provided by handle portion 1600 having an enlarged, curved configuration that can receive at least a thumb or finger of the physician. The enlarged, curved handle portion 1600 may be gripped by the physician while the physician's hand is rested upon a patient during the procedure and/or provide stability during use of the device. Additionally, the combined deployment of locator assembly 1110 and the partial advancement of carrier assembly 1120 in a single step may allow for a reduction in travel of trigger extension 1405. Thus, a user may not need to reach uncomfortably far from handle portion 1600 to trigger extension 1405 to fully advance carrier assembly 1120 and the tube set coupled to the carrier assembly 1120.

Upon reaching the first predetermined position, tube set 305 may be disposed substantially adjacent to outer surface 620a of blood vessel wall 620 that is adjacent to opening 610 such that the blood vessel wall 620 adjacent to opening 610 may be disposed substantially between expanded distal region 210b of locator assembly 200 and tube set 305. Support member 340 may decouple from carrier member 310 and pusher member 320 in the manner described above when tube set 305 is in the first predetermined position. The cover member 330 and pusher member 320 may be advanced. After advancement, the cover member 330 may decouple from the carrier member 310 and pusher member 320. Thereby, cover member 330 and support member 340 may be inhibited from further axial movement and remain substantially stationary as carrier member 310 and pusher member 320 may each remain coupled and axially slidable.

As shown in FIG. 20G, cover member 330 and support member 340 may remain substantially stationary while carrier member 310 and pusher member 320 may continue distally and approach the second predetermined position. As carrier member 310 and pusher member 320 distally advance toward the second predetermined position, annular cavity 370 may move distally relative to substantially-stationary cover member 330 such that distal end region of cover member 330 may no longer enclose annular cavity 370. Thereby, closure element 500 may not be completely enclosed by annular cavity 370 formed by distal end regions of carrier member 310, pusher member 320, and cover member 330.

Although not completely enclosed by annular cavity 370, substantially tubular closure element 500 may be advantageously retained on outer periphery of carrier member 310 by distal end region of cover member 330, as illustrated in FIG. 20G. For example, by retaining substantially tubular closure element 500 between distal end region of cover member 330 and distal end region of carrier member 310, apparatus 100 may be configured to provide improved tissue penetration. The timing between the deployment of substantially tubular closure element 500 by tube set 305 and the retraction and transition to the unexpanded state by locator assembly 200 likewise may be facilitated because substantially tubular closure element 500 is retained between distal end region and distal end region of carrier member 310. Further, carrier member 310 and cover member 330 may operate to maintain substantially tubular closure element 500 in the tubular configuration.

When tube set 305 is in the second predetermined position, carrier member 310 may decouple from pusher member 320 in the manner described in detail above. Therefore, carrier member 310, cover member 330, and/or support member 340 may be inhibited from further axial movement and remain substantially stationary, whereas, pusher member 320 may remain axially slidable. As pusher member 320 continues distally, distal end region of pusher member 320 may contact substantially tubular closure element 500 and may displace substantially tubular closure element 500 from space 360 as shown in FIG. 20H. Since the annular cavity 370 is substantially radially exposed, pusher member 320 may direct substantially tubular closure element 500 over the distally-increasing cross-section of distal end region of substantially-stationary carrier member 310 such that the cross-section of substantially tubular closure element 500 may begin to radially expand. In some embodiments, the radial expansion may be substantially uniform. As substantially tubular closure element 500 traverses the distally-increasing cross-section of distal end region of carrier member 310, the cross-section of substantially tubular closure element 500 may radially expand beyond natural cross-section of closure element 500, as shown in FIGS. 19A-19G.

Upon being directed over the distally-increasing cross-section of the distal end region by pusher member 320, substantially tubular closure element 500 is distally deployed as illustrated in FIG. 20I. When substantially tubular closure element 500 is deployed, tines 520 may pierce and otherwise engage significant amount of blood vessel wall 620 and/or tissue 630 adjacent to opening 610. For example, tines 520 may engage significant amount of blood vessel wall 620 and/or tissue 630 because cross-section 530 of substantially tubular closure element 500 may be expanded beyond natural cross-section 530 of closure element 500 during deployment.

As the closure element is being deployed from the space, locator assembly 200 may begin to retract proximally and locator release system 490 may be activated to transition from the expanded state to the unexpanded state as substantially tubular closure element 500 is deployed. Distal end region 210b of locator assembly 200 may retract proximally and/or transition from the expanded state to the unexpanded state substantially simultaneously with the deployment of substantially tubular closure element 500. As desired, distal end region 210b may be configured to draw blood vessel wall 620 and/or tissue 630 adjacent to opening 610 proximally and into the channel defined by substantially tubular closure element 500. Tines 520 of substantially tubular closure element 500 thereby may pierce and/or otherwise engage blood vessel wall 620 and/or tissue 630.

Turning to FIG. 20J, substantially tubular closure element 500, once deployed, may begin to transition from the tubular configuration, returning to the natural, planar configuration with opposing tines 520 and a natural cross-section of closure element 500. In the present embodiment, substantially tubular closure element 500 may substantially uniformly transition from the tubular configuration to the natural, planar configuration. Rotating axially inwardly to form opposing tines 520 of the closure element 500, tines 520 may draw the tissue into the channel as substantially tubular closure 500" element forms closure element 500. Also, the tissue may be drawn substantially closed and/or sealed as the cross-section of substantially tubular closure element 500 contracts to return to the natural cross-section.

The deployment of the closure element 500 may be monitored, as described above. For example, a user may determine if the closure element 500 is properly positioned as it proceeds within the cover member 330. Interaction between the carrier member 310, the pusher member 320, the cover member 330, and/or the support member 340 may also be monitored.

It will be appreciated that the closure element 500 may be constructed of other materials, that it may include alternative shapes, and that it may adopt alternative methods of operation such that the closure element achieves closure of openings in blood vessel walls or other body tissue. In an additional non-limiting example, the closure element 500 is constructed of materials that use a magnetic force to couple a pair of securing elements in order to close an opening in the lumen wall or tissue. In this alternative embodiment, the closure element 500 may be of a unitary or multi-component construction having a first securing element positionable at a first position adjacent the opening, and a second securing element positionable at a second position adjacent the opening. The first and second securing elements are provided having a magnetic force biasing the first and second securing elements together, thereby closing the opening, or they are provided having a magnetic force biasing both the first and second securing elements toward a third securing element positioned in a manner to cause closure of the opening. The magnetic closure element may be provided without tines, provided the magnetic force coupling the closure elements 500 is sufficient to close the opening. Alternatively, the closure element 500 may be provided with a combination of the magnetic securing elements and tines to provide a combination of coupling forces. Those skilled in the art will recognize that other and further materials, methods, and combinations may be utilized to construct the closure element 500 to achieve the objectives described and implied herein.

FIG. 21 illustrates an embodiment of a stent delivery apparatus 2000. The stent delivery apparatus 2000 may include a balloon catheter 2010. The balloon catheter 2010 may include a balloon 2012 upon which an implantable device, a stent 2020 in the present embodiment, may be carried. In use, a guidewire 2030 may be inserted through the stent delivery apparatus 2000.

The stent may be positioned relative to (within, in the present embodiment) the stent delivery apparatus 2000. The stent 2020 may be in a collapsed state while carried by the balloon 2012 and expanded to a deployed state when properly positioned within a patient.

It may be desirable to position the stent 2020 within a range of distances from the center of the balloon 2012. For example, it may be less desirable to position the stent 2020 off of an edge (not shown) and/or on a shoulder (not shown) of the balloon 2012. Notwithstanding the present discussion, it is appreciated that other possible delivery modes for the stent 2020 are also contemplated, and as such, no intention is made here to limit the present invention to only the above-described stent deployment system.

The methods 10, 20, 40, 60 described above may be used with the present embodiment and/or other embodiments of a stent delivery apparatus 2000. Prior to deployment, it may be determined whether the stent delivery apparatus 2000 is ready for deployment. For example, the relative position of the stent 2020 within the stent delivery apparatus 2000 may be determined. Likewise, it may be determined whether the stent 2020 deployed. Furthermore, the deployment of the stent 2020 may be monitored. Other aspects of the methods 10, 20, 40, 60 may also be practiced with a stent delivery apparatus 2000 and stent 2020.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

I claim:

1. A method for imaging a delivery system to determine if a delivery apparatus, having an implantable vascular closure device, is acceptable for use in deploying the implantable vascular closure device into a patient, the method comprising:
    positioning an implantable vascular closure device within a delivery apparatus, the implantable vascular closure device comprising a first base material that includes a mixture of which a first radiopaque material is a component and/or coating at least a portion of the first base material with a coating of which the first radiopaque material is a component, the delivery device including an obstruction;
    positioning the delivery apparatus within an alignment fixture and relative to an imaging device and outside of the patient;
    analyzing an image produced by the imaging device to identify the obstruction in the delivery apparatus to obstruct deployment of the implantable vascular closure device and/or any defects in at least one component of the delivery apparatus; and
    determining whether the delivery apparatus, having the implantable vascular closure device, is acceptable for use to deploy the implantable vascular closure device into a patient.

2. The method of claim 1, wherein determining whether the delivery apparatus is acceptable for use to deploy an implantable vascular closure device further comprises:
    determining the relative position of the implantable vascular closure device within the delivery apparatus; and
    determining whether the implantable vascular closure device is properly positioned within the delivery apparatus.

3. The method of claim 1, further comprising:
    repositioning the implantable vascular closure device relative to the delivery apparatus if it is determined that the delivery apparatus is not acceptable for use to deploy the implantable vascular closure device into the patient.

4. The method of claim 1, wherein positioning the delivery apparatus relative to the imaging device further comprises aligning the delivery apparatus with at least one alignment indicator associated with the alignment fixture.

5. The method of claim 1, further comprising processing at least one of a portion of a locator assembly and a portion of a carrier assembly configured to carry the implantable device.

6. The method of claim 5, wherein the first radiopaque material and a second radiopaque material are different materials.

7. The method of claim 5, further comprising processing a second portion of the delivery apparatus by providing a second base material that includes a mixture of which a second radiopaque material is a component and/or coating at least a portion of the second base material with a coating of which the second radiopaque material is a component.

8. The method of claim 7, wherein at least one of the first radiopaque material, a second radiopaque material, and the third radiopaque material have different radiopacities.

9. The method of claim 5, wherein the portion of the locator assembly that is processed is at least one of a portion of a tubular body and a portion of a control member.

10. The method of claim 9, wherein the portion of the tubular body that is processed is at least one of a portion of a distal end of the tubular body and a portion of an expansion end of the tubular body.

11. The method of claim 10, wherein the portion of the expansion end of the tubular body that is processed is a portion of at least one substantially flexible member of the expansion end.

12. The method of claim 5, wherein the portion of the carrier assembly that is processed is a portion of a tube set.

13. A method for determining whether an implantable device deployed, the method comprising:
   positioning a delivery apparatus within an alignment fixture having at least one alignment indicator and relative to an imaging device, the delivery apparatus having at least a portion that is capable of being imaged by an imaging device, the delivery apparatus comprising an implantable device positioned within the delivery apparatus, the implantable device being capable of being imaged by an imaging device;
   analyzing a first image produced by the imaging device to identify any obstructions in the delivery apparatus to obstruct deployment of the implantable device and/or any defects in at least one component of the delivery apparatus;
   determining the relative position of the implantable device within the delivery apparatus and relative to the at least one alignment indicator;
   deploying the implantable device from the delivery apparatus;
   after deploying the implantable device from the delivery apparatus, removing the delivery apparatus from the patient and then positioning the delivery apparatus within the alignment fixture having the at least one alignment indicator and relative to the imaging device following deployment of the implantable device;
   analyzing a second image produced by the imaging device; and
   determining whether the implantable device was deployed by determining whether the implantable device is viewable in the second image.

14. The method of claim 13, wherein positioning the delivery apparatus further comprises aligning the delivery apparatus with the least one alignment indicator.

15. The method of claim 13, further comprising after deploying the implantable device, determining the position of the implantable device within the delivery apparatus.

16. The method of claim 15, further comprising determining the position of at least one delivery apparatus component.

17. The method of claim 16, wherein determining the position of at least one delivery apparatus component further comprises determining the position of a portion of a control member.

18. The method of claim 16, wherein determining the position of at least one delivery apparatus component further comprises determining the position of a portion of a locator assembly.

19. The method of claim 16, wherein determining the position of at least one delivery apparatus component further comprises determining the position of a portion of a carrier assembly.

20. A method for imaging a delivery system for use with a patient, the method comprising:
   forming an implantable vascular closure device from a first base material;
   processing the implantable vascular closure device by providing the first base material that includes a mixture of which a first radiopaque material is a component and/or coating at least a portion of the first base material with a coating of which the first radiopaque material is a component;
   forming at least a portion of a delivery apparatus from a second base material;
   processing at least a portion of the delivery apparatus by providing the second base material that includes a mixture of which a second radiopaque material is a component and/or coating at least a portion of the second base material with a coating of which the second radiopaque material is a component;
   positioning the implantable vascular closure device within the delivery apparatus, the delivery device including an obstruction;
   positioning the delivery apparatus within an alignment fixture and relative to an x- ray imaging device and outside of the patient;
   analyzing an image produced by the x-ray imaging device to identify the obstruction in the delivery apparatus to obstruct deployment of the implantable vascular closure device and/or any defects in at least one component of the delivery apparatus;
   determining the relative position of the implantable vascular closure device within the delivery apparatus;
   determining whether the implantable vascular closure device is properly positioned within the delivery apparatus;
   deploying the implantable vascular closure device;
   during the deployment of the implantable vascular closure device, monitoring the relative position and/or velocity of the implantable vascular closure device within the delivery apparatus using the x-ray imaging device;
   after deploying the implantable vascular closure device from the delivery apparatus, removing the delivery apparatus from the patient and then positioning the delivery apparatus within the alignment fixture having the at least one alignment indicator and relative to the x-ray imaging device following deployment of the implantable vascular closure device;
   analyzing an image produced by the x-ray imaging device;
   determining whether the implantable vascular closure device was deployed and, determining the position of the implantable vascular closure device within the delivery apparatus if the implantable vascular closure device was not deployed; and
   determining the position of at least one delivery apparatus component.

* * * * *